United States Patent [19]

Cady et al.

[11] Patent Number: 5,891,840
[45] Date of Patent: Apr. 6, 1999

[54] STABILIZATION OF SOMATOTROPINS BY MODIFICATION OF CYSTEINE RESIDUES UTILIZING SITE DIRECTED MUTAGENESIS

[75] Inventors: Susan Mancini Cady, Yardley, Pa.; John Steele Logan, Robbinsville, N.J.; Brian Lee Buckwalter; Gerald William Stockton, both of Yardley, Pa.; Deborah Tardy Chaleff, Pennington, N.J.

[73] Assignee: American Cyanamid Company, Wayne, N.J.

[21] Appl. No.: 437,578

[22] Filed: May 9, 1995

Related U.S. Application Data

[63] Continuation of Ser. No. 960,073, Oct. 13, 1992, abandoned, which is a continuation of Ser. No. 372,699, Jul. 3, 1989, abandoned, which is a continuation-in-part of Ser. No. 236,060, Aug. 24, 1988, abandoned.

[51] Int. Cl.$^6$ ............................ A61K 38/27; C07K 14/61
[52] U.S. Cl. ................................ 514/2; 514/21; 530/399; 424/423
[58] Field of Search ..................... 530/399; 514/2, 514/12, 21; 435/69.4; 424/423

[56] References Cited

U.S. PATENT DOCUMENTS

| | | | |
|---|---|---|---|
| 4,443,539 | 4/1984 | Fraser et al. | 435/69.4 |
| 4,761,289 | 8/1988 | Shalati et al. | 424/468 |
| 4,774,091 | 9/1988 | Yamahira et al. | 424/426 |
| 4,959,314 | 9/1990 | Mark et al. | 435/69.1 |
| 5,079,230 | 1/1992 | Randawa et al. | 514/12 |

FOREIGN PATENT DOCUMENTS

| | | |
|---|---|---|
| 0109748 | 5/1984 | European Pat. Off. |
| 0146354 | 6/1985 | European Pat. Off. |
| WO 92/01789 | 2/1992 | WIPO . |

OTHER PUBLICATIONS

Graf et al., FEBS LETTERS, 66(2):233–237 (Jul. 1976).
Bewley et al., Short Communications, Biochim. Biophys. Acta, 154:420–422 (1968).
A. Klibanov, "Stabilization of Enzymes Against Thermal Inactivation," Advances in Applied Microbiology, 29:14–15 and 22 (1983).
T. Bewley et al., Biochemistry, 8:4701–4708 (1969).
J. Mills et al., Annals New York Acad. Sci., 148:343–351 (1968).
Tokunaga et al., Eur. J. Biochem. 153:445–449 (1985).
Wang et al., Science, 224:1431–1433 (1984).
Graf et al., Int. J. Peptide Protein Res., 7:467–473 (1975).
Necessary et al., Biol. Abstract No. 80:002951, and Mol. Cell. Endocrinol., 39(3):247–254 (1985).
Creighton, Proteins: Structure and Molecular Properties, W.H. Freeman & Co., New York, (1984) pp. 1–24.
Seeburg et al., DNA, 2(1):37–45 (1983).
Wang et al., J. Parenteral Sci. & Tech., Supplement, vol. 42, 2S, Technical Report No. 10 (1988).
Kenney et al. (1986) Lymphokine Res. 5, 523–527.

*Primary Examiner*—Charles L. Patterson, Jr.
*Assistant Examiner*—Keith D. Hendricks
*Attorney, Agent, or Firm*—Darryl L. Webster; M. Paul Barker

[57] ABSTRACT

Novel modified or derivatized recombinant animal somatotropins. Methods for stabilizing recombinant animal somatotropins by modification or deletion of the Cysteine residues utilizing site directed mutagenesis to replace from one to four of the cysteine amino acid residues of said somatotropins with one or more different amino acid residues or by derivatization of (1) both cysteine amino acid residues in the small loop of said somatotropin, both cysteine amino acid residues in the large loop or the four cysteine amino acid residues in both loops of said somatotropin.

19 Claims, 8 Drawing Sheets

STABILIZATION OF SOMATOTROPINS BY MODIFICATION OF CYSTEINE RESIDUES UTILIZING SITE DIRECTED MUTAGENESIS

This application is a continuation of application Ser. No. 07/960,073, filed Oct. 13, 1992, now abandoned, which is a continuation of application Ser. No. 07/372,699 filed on Jul. 3, 1989, now abandoned, which is a continuation-in-part of Ser. No. 07/236,060, filed on Aug. 24, 1988, now abandoned.

BACKGROUND OF THE INVENTION

The present invention relates to novel modified or derivatized recombinant animal somatotropins wherein at least one (1) of the four (4) cysteine amino acids residues of said recombinant animal somatotropins is replaced, modified, deleted or derivatized. Although somatotropins have been and continue to be recombinantly produced, oftentime those somatotropins are difficult to formulate in order to effectively administer to an animal. Unlike such expressed somatotropins, it has been discovered that the alteration or elimination of the cysteine residues, four of which exist in somatotropins, either by substitution by another amino acid or by derivatization of the cysteines, results in biologically active compounds with enhanced stability to formulate in acceptable fashions in order to administer to animals.

It is the object of the present invention, therefore, to provide novel animal somatotropins wherein at least one (1) of the cysteine residues of the somatotropin has been replaced by another amino acid, modified, deleted or chemical derivatized. It is a further object of the invention to substitute and/or derivatize two (2), three (3) or all four (4) of the cysteine residues of animal somatotropins and provide those novel compounds. Two cysteines are in the small loop and two are in the large loop.

Also, another object of the present invention is to provide compositions of said substituted, replaced (modified), eliminated and/or derivatized animal somatotropins which are biologically effective and yet stable to administer. It is another object of the present invention to provide compositions of biologically active recombinant animal somatotropins which are suitable for parenteral administration comprising a growth promoting amount of a modified or derivatized recombinant animal somatotropin or pharmaceutically and pharmacologically acceptable salt thereof in a pharmaceutically and pharmacologically acceptable solid or liquid carrier, wherein the growth rate of an animal is increased over an extended period of time of five days or more.

These and other objects of the invention will become apparent by the more detailed description of the invention provided hereinbelow.

SUMMARY OF THE INVENTION

The present invention relates to novel modified (substituted or eliminated cysteine(s)) or derivatized recombinant animal somatotropins in which from one to four of the cysteine amino acid residues of said somatotropins are replaced by from one to four amino acid residues, separately selected from the amino acids, arginine, lysine, aspartic acid, glutamic acid, asparagine, glutamine, histidine, alanine, glycine, isoleucine, leucine, valine, phenylalanine, tryptophan, tyrosine, methionine, serine, threonine or proline; or in which all four cysteines are converted to cysteic acid; or in which both cysteines in the small loop or both cysteines in the large loop or all four cysteines in both said loops are derivatized with substituents selected from $(CH_2COOH)$, $[CH(CO_2H)(CH_2)_xCO_2H]$, $(CH_2CONR_3R_4)$, $(R_5)$, $[(CH_2)_nSO_3]$, $(CHCH_2CONR_3CO)$, $(CH_2)_mNR_3R_4$, $(CH_2OCOCH_2R_5)$, or $(SR_6)$; wherein $R_3$ and $R_4$ are each H, $[(CH_2)_xCO_2H]$, $[CH(CO_2H)(CH_2)_xCO_2H]$, $C_1$–$C_6$ alkyl optionally substituted with from 0 to 2 hydroxyl groups, or polyethylene glycol; $R_5$ is $C_1$–$C_6$ alkyl or $C_1$–$C_4$ alkoxymethyl and $R_6$ is $C_1$–$C_6$ alkyl, polyethylene glycol or phenyl optionally substituted with one or two carboxylic acid or sulfonic acid groups; n is an integer of from 0 to 4, m is an integer of from 2 to 4; and x is an integer of from 1 to 3; provided that when the cysteine amino acid residues of said recombinant animal somatotropin are derivatized, both cysteine residues in the small loop or both cysteine residues in the large loop of said somatotrotropin are substituted with the same group; provided also that the substituents on the cysteine residues in the small loop (Lable and closest to C-terminus) may be the same or different substituents than those on the cysteines of the large loop (stable and closest to N-terminus) and further provided that when one cysteine amino acid residue is oxidized to cysteic acid, all said cysteine residues in said somatotropin are oxidized to cysteic acid.

The present invention also provides methods for inhibiting aggregation of recombinant animal somatotropin by substituting one or more of the cysteine amino acid residues located at the 55, 166, 183 or 191 positions of a recombinant animal somatotropin with arginine, lysine, aspartic acid, glutamic acid, asparagine, glutamine, histidine, alanine, glycine, isoleucine, leucine, valine, phenylalanine, tryptophan, tyrosine, methionine, serine, threonine or proline, or oxidizing all four of said cysteine residues to cysteic acid.

This invention further relates to a method for inhibiting aggregation of recombinant animal somatotropin, by reducing at least one of the two disulfide bridges between the cysteine amino acid residues at the 55 and 166 positions or at the 183 and 191 positions of said somatotropins and thereafter derivatizing each of the cysteines of the reduced bridge or bridges at the 55 and 166 positions and/or at the 183 and 191 positions with the same derivative, provided that the derivatives on the cysteines at the 55 and 166 positions may be the same or different substituents than the substituents on the cysteines at the 183 and 191 positions. The substituents employed in the preparation of the novel derivatized recombinant animal somatotropins of this invention include the following: $(CH_2COOH)$, $[CH(CO_2H)(CH_2)_xCO_2H]$, $(CH_2CONR_3R_4)$, $(R_5)$, $[(CH_2)_nSO_3]$, $(SR_6)$, $(CHCH_2CONR_3CO)$, $(CH_2)_m$, $NR_3R_4$, or $(CH_2OCOH_2R_5)$, wherein $R_3$ and $R_4$ are each H, $[(CH_2)_xCO_2H]$, $[CH(CO_2H)(CH_2)_xCO_2H]$, $C_1$–$C_6$ alkyl optionally substituted with from 0 to 2 hydroxyl groups, or polyethylene glycol; $R_5$ is $C_1$–$C_6$ alkyl or $C_1$–$C_4$ alkoxymethyl; $R_6$ is $C_1$–$C_6$ alkyl, polyethylene glycol or phenyl optionally substituted with one or two carboxylic acid or sulfonic acid groups; n is an integer of from 0 to 4; and m is an integer of from 2 to 4 and x is an integer of from 1 to 3.

In accordance with the present invention, the preferred novel animal somatotropins are recombinant porcine, bovine, ovine, human and avian somatotropins wherein the disulfide bridge in the small loop of the somatotropin is reduced and the cysteines at the 183 and 191 positions derivatized with a substituent selected from $(CH_2COOH)$, $[CH(CO_2H)(CH_2)_xCO_2H]$, $(CH_2CONR_3R_4)$, $(R_5)$, $(CH_2)_nSO_3$ or $(SR_6)$; wherein $R_3$, $R_4$ $R_5$, $R_6$, n and x are as described.

Also, the cysteines are eliminated from one cysteine to all four.

All of the plasmids, DNA sequences and microorganisms deposited in connection with the present patent application, except where specifided to the contrary, are deposited in American Cyanamid Company culture collection maintained in Princeton, N.J. and are deposited with the American Type Culture Collection (ATCC) in Rockville, Md. 20952, U.S.A.

BRIEF DESCRIPTION OF THE FIGURES

FIG. 5: Schematic representation of the construction of the bacterial expression vector containing the mutated pST gene. The plasmids confer resistance to the antibiotic ampicillin ($amp^R$).

DETAILED DESCRIPTION OF THE INVENTION

Figure 1A:
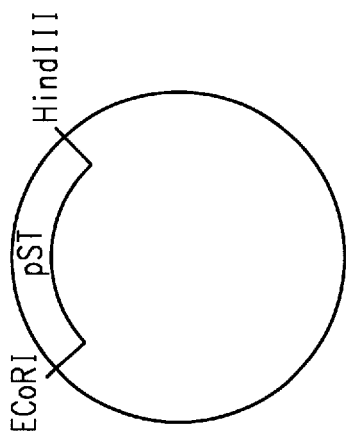
FIG. 1: Cloning of the porcine somatotropin gene into M13mp11. M13mp11 RF DNA is cut with the restriction enzymes ECORI and HindIII, treated with calf intestinal alkaline phosphatase. The expression plasmid pEFF-902 is digested with the restriction enzymes ECoRI and HindIII. The appropriate fragments are purified after electrophoresis on a 1% agarose gel. The purified fragments are ligated and transformed into E. coli JM101. The structure of the resultant M13mp11pST-RF DNA is illustrated.
Figure 1B:
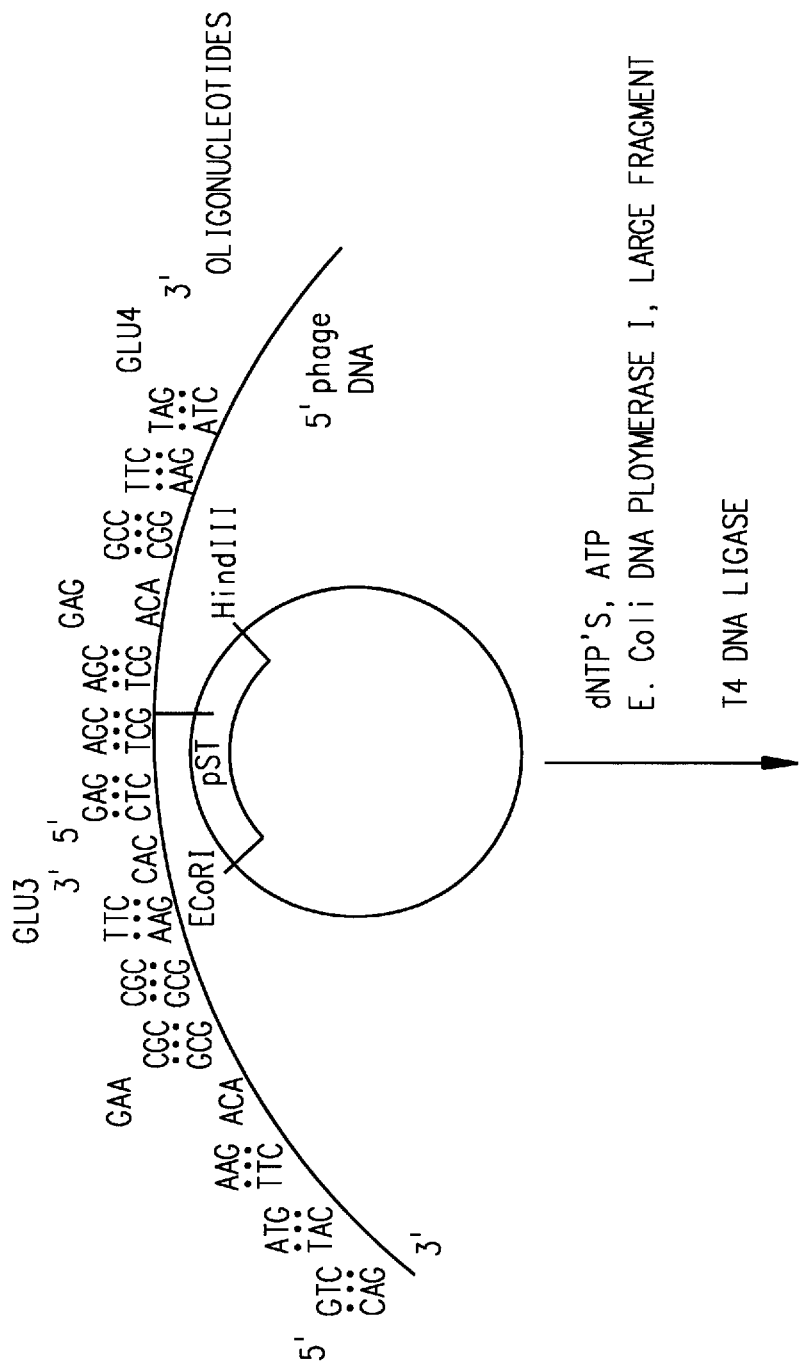
Figure 1C:
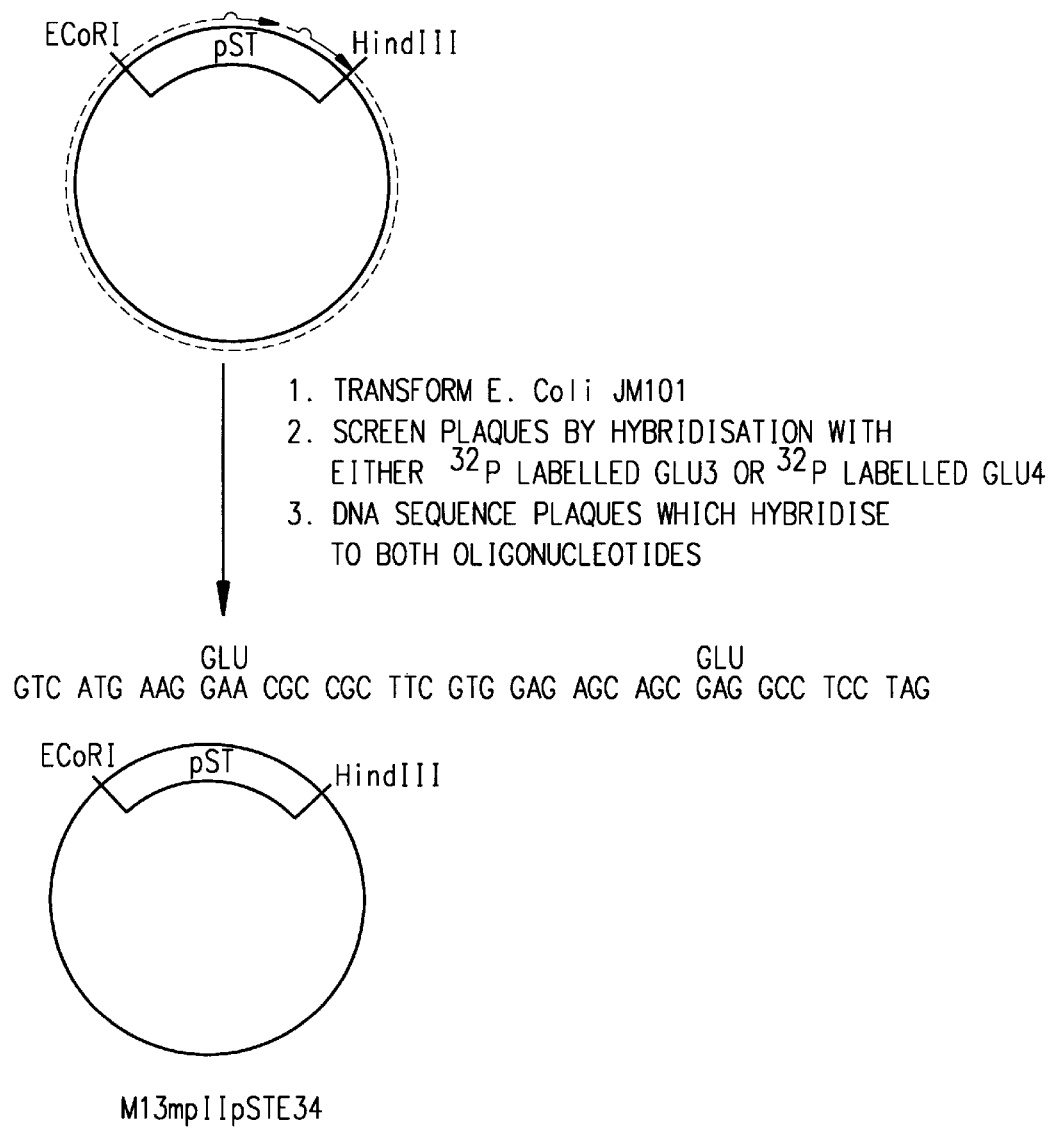

Preferred modified recombinant animal somatotropins of this invention are illustrated hereinbelow, but recombinantly-derived somatotropins without the additional Asp-Gln additional substitutions or with other substitutions are prepared in accordance with the present invention, as well. Further animal somatotropins with deletions in amino acid chain length, additions to amino acid chain length, replacement of amino acids (besides cysteines), fragments with the active portion and the like are all within the scope of the present invention. Numbering of amino acid residues herein related to the Met-Asp-Gln analogues, but numbering is altered accordingly by one skilled in the art in order to identify the disulfide bridges formed by the four cryteine residues.

Recombinant Porcine Somatotropin

H — Met — Asp — Gln — Phe — Pro — Ala — Met — Pro — Leu — Ser — Ser —

Leu — Phe — Ala — Asn — Ala — Val — Leu — Arg — Ala — Gln — His — Leu —

His — Gln — Leu — Ala — Ala — Asp — Thr — Tyr — Lys — Glu — Phe — Glu —

Arg — Ala — Tyr — Ile — Pro — Glu — Gly — Gln — Arg — Tyr — Ser — Ile —
                                                                    55

Gln — Asn — Ala — Gln — Ala — Ala — Phe — $R_2$ — Phe — Ser — Glu — Thr —

Ile — Pro — Ala — Pro — Thr — Gly — Lys — Asp — Glu — Ala — Gln — Gln —

Arg — Ser — Asp — Val — Glu — Leu — Leu — Arg — Phe — Ser — Leu — Leu —

Leu — Ile — Gln — Ser — Trp — Leu — Gly — Pro — Val — Gln — Phe — Leu —

Ser — Arg — Val — Phe — Thr — Asn — Ser — Leu — Val — Phe — Gly — Thr —

Ser — Asp — Arg — Val — Tyr — Glu — Lys — Leu — Lys — Asp — Leu — Glu —

Glu — Gly — Ile — Gln — Ala — Leu — Met — Arg — Glu — Leu — Glu — Asp —

Gly — Ser — Pro — Arg — Ala — Gly — Gln — Ile — Leu — Lys — Gln — Thr —

Tyr — Asp — Lys — Phe — Asp — Thr — Asn — Leu — Arg — Ser — Asp — Asp —
                                                                    166

Ala — Leu — Leu — Lys — Asn — Tyr — Gly — Leu — Leu — Ser — $R_{2a}$ — Phe —

Lys — Lys — Asp — Leu — His — Lys — Ala — Glu — Thr — Tyr — Leu — Arg —
         183                                                        191

Val — Met — Lys — $R_1$ — Arg — Arg — Phe — Val — Glu — Ser — Ser — $R_{1a}$ —

Ala — Phe — OH.

Recombinant Bovine Somatotropin

H — Met — Asp — Gln — Phe — Pro — Ala — Met — Ser — Leu — Ser — Gly —

Leu — Phe — Ala — Asn — Ala — Val — Leu — Arg — Ala — Gln — His — Leu —

His — Gln — Leu — Ala — Ala — Asp — Thr — Phe — Lys — Glu — Phe — Glu —

Arg — Thr — Tyr — Ile — Pro — Glu — Gly — Gln — Arg — Tyr — Ser — Ile —
                                                                    55

-continued
Recombinant Porcine Somatotropin

Gln—Asn—Thr—Gln—Val—Ala—Phe—$R_2$—Phe—Ser—Glu—Thr—

Ile—Pro—Ala—Pro—Thr—Gly—Lys—Asn—Glu—Ala—Gln—Gln—

Lys—Ser—Asp—Leu—Glu—Leu—Leu—Arg—Ile—Ser—Leu—Leu—

Leu—Ile—Gln—Ser—Trp—Leu—Gly—Pro—Leu—Gln—Phe—Leu—

Ser—Arg—Val—Phe—Thr—Asn—Ser—Leu—Val—Phe—Gly—Thr—

Ser—Asp—Arg—Val—Tyr—Glu—Lys—Leu—Lys—Asp—Leu—Glu—

Glu—Gly—Ile—Leu—Ala—Leu—Met—Arg—Glu—Leu—Glu—Asp—

Gly—Thr—Pro—Arg—Ala—Gly—Gln—Ile—Leu—Lys—Gln—Thr—

Tyr—Asp—Lys—Phe—Asp—Thr—Asn—Met—Arg—Ser—Asp—Asp—
                                                                166

Ala—Leu—Leu—Lys—Asn—Tyr—Gly—Leu—Leu—Ser—$R_{2a}$—Phe—

Arg—Lys—Asp—Leu—His—Lys—Thr—Glu—Thr—Tyr—Leu—Arg—
            183                                              191

Val—Met—Lys—$R_1$—Arg—Arg—Phe—Gly—Glu—Ala—Ser—$R_{1a}$—

Ala—Phe—OH.

Recombinana Ovine Somatotropin

H—Met—Asp—Gln—Phe—Pro—Ala—Met—Ser—Leu—Ser—Gly—

Leu—Phe—Ala—Asn—Ala—Val—Leu—Arg—Ala—Gln—His—Leu—

His—Gln—Leu—Ala—Ala—Asp—Thr—Phe—Lys—Glu—Phe—Glu—

Arg—Thr—Tyr—Ile—Pro—Glu—Gly—Gln—Arg—Tyr—Ser—Ile—
                        55

Gln—Asn—Thr—Gln—Val—Ala—Phe—$R_2$—Phe—Ser—Glu—Thr—

Ile—Pro—Ala—Pro—Thr—Gly—Lys—Asp—Glu—Ala—Gln—Gln—

Lys—Ser—Asp—Leu—Glu—Leu—Leu—Arg—Ile—Ser—Leu—Leu—

Leu—Ile—Gln—Ser—Trp—Leu—Gly—Pro—Leu—Gln—Phe—Leu—

Ser—Arg—Val—Phe—Thr—Asn—Ser—Leu—Val—Phe—Gly—Thr—

Ser—Asp—Arg—Val—Tyr—Glu—Lys—Leu—Lys—Asp—Leu—Glu—

Glu—Gly—Ile—Leu—Ala—Leu—Met—Arg—Glu—Leu—Glu—Asp—

Val—Thr—Pro—Arg—Ala—Gly—Gln—Ile—Leu—Lys—Gln—Thr—

Tyr—Asp—Lys—Phe—Asp—Thr—Asn—Met—Arg—Ser—Asp—Asp—
                                                                166

Ala—Leu—Leu—Lys—Asn—Tyr—Gly—Leu—Leu—Ser—$R_{2a}$—Phe—

Arg—Lys—Asp—Leu—His—Lys—Thr—Glu—Thr—Tyr—Leu—Arg—
            183                                              191

Val—Met—Lys—$R_1$—Arg—Arg—Phe—Gly—Glu—Ala—Ser—$R_{1a}$—

Ala—Phe—OH.

Recombinant Horse Somatotripin

H—Met—Asp—Gln—Phe—Pro—Ala—Met—Pro—Leu—Ser—Ser—

Leu—Phe—Ala—Asn—Ala—Val—Leu—Arg—Ala—Gln—His—Leu—

His—Gln—Leu—Ala—Ala—Asp—Thr—Tyr—Lys—Glu—Phe—Glu—

Arg—Ala—Tyr—Ile—Pro—Glu—Gly—Gln—Arg—Tyr—Ser—Ile—
                        55

Gln—Asn—Ala—Gln—Ala—Ala—Phe—$R_2$—Phe—Ser—Glu—Thr—

Recombinant Porcine Somatotropin

Ile—Pro—Ala—Pro—Thr—Gly—Lys—Asp—Glu—Ala—Gln—Gln—

Arg—Ser—Asp—Met—Glu—Leu—Leu—Arg—Phe—Ser—Leu—Leu—

Leu—Ile—Gln—Ser—Trp—Leu—Gly—Pro—Val—Gln—Leu—Leu—

Ser—Arg—Val—Phe—Thr—Asn—Ser—Leu—Val—Phe—Gly—Thr—

Ser—Asp—Arg—Val—Tyr—Glu—Lys—Leu—Arg—Asp—Leu—Glu—

Glu—Gly—Ile—Gln—Ala—Leu—Met—Arg—Glu—Leu—Glu—Asp—

Gly—Ser—Pro—Arg—Ala—Gly—Gln—Ile—Leu—Lys—Gln—Thr—

Tyr—Asp—Lys—Phe—Asp—Thr—Asn—Leu—Arg—Ser—Asp—Asp—
                                                166

Ala—Leu—Leu—Lys—Asn—Tyr—Gly—Leu—Leu—Ser—$R_{2a}$—Phe—

Lys—Lys—Asp—Leu—His—Lys—Ala—Glu—Thr—Tyr—Leu—Arg—
            183                                      191

Val—Met—Lys—$R_1$—Arg—Arg—Phe—Val—Glu—Ser—Ser—$R_{1a}$—

Ala—Phe—OH.

Recombinant Human Somatotropin

H—Met—Asp—Gln—Phe—Pro—Thr—Ile—Pro—Leu—Ser—Arg—

Leu—Phe—Asp—Asn—Ala—Met—Leu—Arg—Ala—His—Arg—Leu—

His—Gln—Leu—Ala—Phe—Asp—Thr—Tyr—Gln—Glu—Phe—Glu—

Glu—Ala—Tyr—Ile—Pro—Lys—Glu—Gln—Lys—Tyr—Ser—Phe—
                                    56

Leu—Gln—Asn—Pro—Gln—Thr—Ser—Leu—$R_2$—Phe—Ser—Glu—

Ser—Ile—Pro—Thr—Pro—Ser—Asn—Arg—Glu—Glu—Thr—Gln—

Gln—Lys—Ser—Asn—Leu—Glu—Leu—Leu—Arg—Ile—Ser—Leu—

Leu—Leu—Ile—Gln—Ser—Trp—Leu—Glu—Pro—Val—Gln—Phe—

Leu—Arg—Ser—Val—Phe—Ala—Asn—Ser—Leu—Val—Tyr—Gly—

Ala—Ser—Asp—Ser—Asn—Val—Tyr—Asp—Leu—Leu—Lys—Asp—

Leu—Glu—Glu—Gly—Ile—Gln—Thr—Leu—Met—Gly—Arg—Leu—

Glu—Asp—Gly—Ser—Pro—Arg—Thr—Gly—Gln—Ile—Phe—Lys—

Gln—Thr—Tyr—Ser—Lys—Phe—Asp—Thr—Asn—Ser—His—Asn—

Asp—Asp—Ala—Leu—Leu—Lys—Asn—Tyr—Gly—Leu—Leu—Tyr—
167

$R_{2a}$—Phe—Arg—Lys—Asp—Met—Asp—Lys—Val—Glu—Thr—Phe—
                            184

Leu—Arg—Ile—Val—Gln—$R_1$—Arg—Ser—Val—Glu—Gly—Ser—
191

$R_{1a}$—Gly—Phe—OH.

Recombinant Avian Somatotropin

H—Met—Asp—Gln—Phe—Pro—Ala—Met—Pro—Leu—Ser—Asn—

Leu—Phe—Ala—Asn—Ala—Val—Leu—Arg—Ala—Gln—His—Leu—

His—Leu—Leu—Ala—Ala—Gln—Thr—Tyr—Lys—Glu—Phe—Glu—

Arg—Thr—Tyr—Ile—Pro—Glu—Asp—Gln—Arg—Tyr—Thr—Asn—
                            55

Lys—Asn—Ser—Gln—Ala—Ala—Tyr—$R_2$—Phe—Ser—Glu—Thr—

Ile—Pro—Ala—Pro—Thr—Gly—Lys—Asp—Asp—Ala—Gln—Gln—

Lys—Ser—Asp—Met—Gly—Leu—Leu—Arg—Phe—Ser—Leu—Val—

-continued
Recombinant Porcine Somatotropin

Leu—Ile—Gln—Ser—Trp—Leu—Thr—Pro—Val—Gln—Tyr—Leu—

Ser—Lys—Val—Phe—Thr—Asn—Asn—Leu—Val—Phe—Gly—Thr—

Ser—Asp—Arg—Val—Phe—Glu—Lys—Leu—Lys—Asp—Leu—Glu—

Glu—Gly—Ile—Gln—Ala—Leu—Met—Arg—Glu—Leu—Glu—Asp—

Arg—Ser—Pro—Arg—Gly—Pro—Gln—Leu—Leu—Arg—Pro—Thr—

Tyr—Asp—Lys—Phe—Asp—Ile—His—Leu—Arg—Asn—Glu—Asp—
166

Ala—Leu—Leu—Lys—Asn—Tyr—Gly—Leu—Leu—Ser—$R_{2a}$—Phe—

Lys—Lys—Asp—Leu—His—Lys—Val—Glu—Thr—Tyr—Leu—Lys—
183                                                                191

Val—Met—Lys—$R_1$—Arg—Arg—Phe—Gly—Glu—Ser—Asn—$R_{1a}$—

Thr—Ile—OH.

wherein $R_1$, $R_{1a}$, $R_2$ and $R_{2a}$ of said recombinant animal somatotropins each independently represent amino acid residues selected from arginine, lysine, aspartic acid, glutamic acid, asparagine, glutamine, histidine, alanine, glycine, isoleucine, leucine, valine, phenylalanine, tryptophan, tyrosine, methionine, serine, threonine, proline or cystein; provided that at least one of said amino acid residues represented by $R_1$, $R_{1a}$, $R_2$ and $R_{2a}$ in the above illustrated somatotropins, represents an amino acid residue otherthan cysteine.

Especially preferred modified recombinant animal somatotropins of the invention are those in which one or both of the $R_1$ and $R_{1a}$ substituents at the 183 and 191 positions of the somatotropin or at the 184 and 191 positions of the recombinant human somatotropin represent amino acids other than cysteine.

Site Directed Mutagenesis

Preparation of the above said modified (substituted) recombinant animal somatotropins of this invention are achieved by site directed mutagenesis. Currently utilized techniques for the alteration of the DNA sequence of a cloned segment of DNA at a specific defined site require the production of a single stranded form of that DNA. The single stranded DNA is annealed to a synthetic oligonucleotide which is complementary to a portion of it, except that the oligonucleotide contains within it a region of mismatch. The region of mismatch is usually located in the central portion of the oligonucleotide. The annealed mixture is then made double stranded and covalently closed by the addition of E. coli DNA polymerase I, large fragment and deoxynucleotide triphosphates in the presence of T4 DNA ligase and adenosine 5' triphosphate. The double stranded DNA is then transformed into an appropriate E. coli strain where the mismatched region of the DNA is repaired and replicated. Two populations of clones are obtained. Dependant on which strand is chosen as the template for repair synthesis, a clone either contains the wild type or the altered (mutated) sequence. The clones which contain the mutated sequence, i.e. that which corresponds to the sequence of the oligonucleotide, are selected by hybridisation to the radioactively-labelled oligonucleotide. Due to the mismatch between the oligonucleotide and the wild type sequence, the radioactively-labelled oligonucleotide is more stably bound to the clones which contain the mutated sequence. Incubation at an appropriate temperature therefore differentiates between wild type and mutated clones. The alterations in the identified clones then are confirmed by DNA sequencing of the relevant regions. In the following discussions, recombinant porcine somatotropin is selected as representative of the modified and derivatized recombinant animal somatotropins of the present invention and the methods employed for their preparation.

Cloning of the porcine somatotropin (rpST) gene into the single strand producing vector bacteriophage M13mp11, is achieved by the following general procedure as diagrammed in Figure I.

A fragment of DNA containing the porcine somatotropin (rpST) gene is isolated from the bacterial expression plasmid pEFF-902 by cleavage with the restriction enzymes ECoRI and HindIII. The rpST gene containing fragment is then purified by agarose gel electrophoresis. M13mp11 replicative form (RF) DNA is digested with ECoRI and HindIII, treated with calf intestinal alkaline phosphatase and the large fragment purified by agarose gel electrophoresis. The two purified fragments are then mixed together and ligated with T4 DNA ligase. The mixture is transformed into E. coli JM101 Number 33876 and several of the resultant plaques grown. Replicative form (RF) DNA is prepared by a standard alkaline lysis procedure and the structure determined by digestion with appropriate restriction enzymes. A clone is isolated which contains the expected fragments and is designated M13mp11pST. DNA sequence analysis is used to confirm the identity of the clone.

Figure 2:
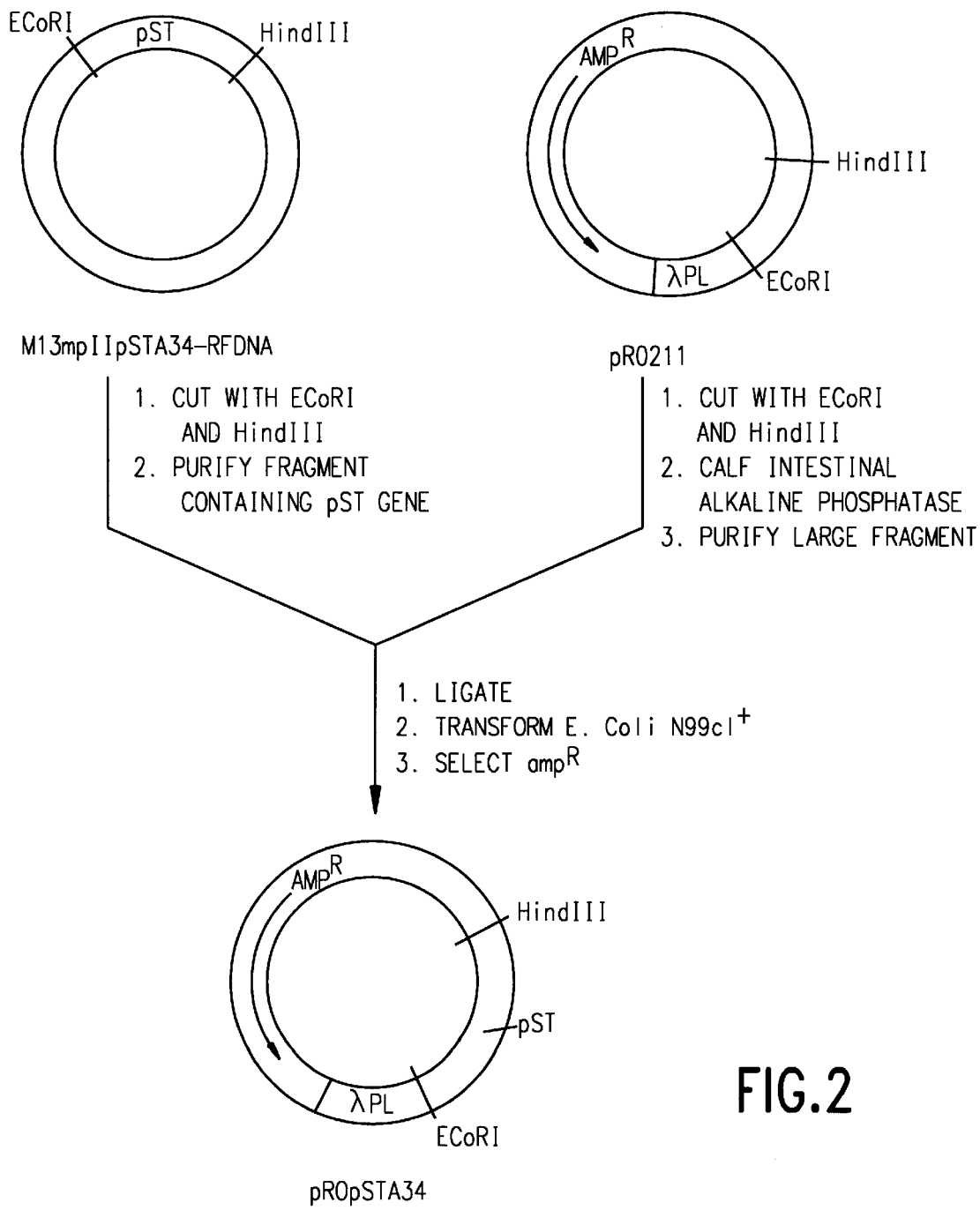
FIG. 2: Schematic representation of the mutagenesis scheme using the AA1 oligonucleotide and M13mp11pST-single stranded DNA.

Mutagenesis of the rpST gene in M13mp11pST is then achieved as described below and diagrammed in FIG. 2. The aim of the mutagenesis program is to generate a rpST molecule incapable of the formation of the small loop disulphide bond, the large loop disulphide bond or both by substitution of the relevant cysteine residues by other amino acids. The large loop disulphide is located between cysteines at positions 55 and 166 in the rpST gene. The small loop disulphide is between cysteines located at 183 and 191. The numbering system is as described. Two basic protocols are used to obtain the required mutants and examples of each are hereinafter described.

In the first method, substitution of the cysteines in the small loop disulphide bond is accomplished using a long synthetic oligonucleotide. In this method the oligonucleotide designated AA1 is employed and has the following sequence: 5' GTC ATG AAG GCG CGC CGC TTC GTG GAG AGC AGC GCT GCC TTC TAG 3'

This alters the sequence of the pST gene such that the codon for cysteine at position 183 is converted from TGT to GCG which codes for alanine and the cysteine at position 191 is converted from TGT to GCT which also codes for alanine. Therefore, the cysteines in the small loop are both converted to alanine. Single stranded M13mp11pST DNA is prepared from purified phage by standard protocols. Diagrammed in FIG. 2 is the outline of the mutagenesis method. 1000 ng of single stranded M13mp11pST DNA is mixed with 50 ng of AA1 oligonucleotide, which has previously been 5' phosphorylated with adenosine 5' triphosphate and polynucleotide kinase. The mixture is heated at 65° C. for 7 minutes and then kept at room temperature for 10 minutes. This protocol anneals the oligonucleotide to the single standed DNA. The annealed DNA is then converted to a double stranded covalently closed form by the addition of ATP, dNTP's (a mixture of the four deoxyribonucleotide 5' triphosphates), T4 DNA ligase and DNA polymerase I large fragment. The mixture is incubated for 1 hour at room temperature. The mixture is then transformed into E. coli JM101 by a standard calcium chloride procedure. After overnight incubation at 37° C., plaques are seen on a lawn of JM101. The plaques are lifted onto nitrocellulose filters and processed for hybridisation by standard protocols. A second oligonucleotide designated AA1D is used for detection of the mutants. AA1D has the following sequence 5' C ATG AAG GCG CGC CGC TT 3'. It is radioactively labelled at the 5' end with c-$^{32}$P-ATP and polynucleotide kinase. Hybridisation is overnight at 37° C. in 5×SSC (1×SSC is 0.15M sodium chloride, 0.015M sodium citrate pH7.0), 1× Denhardt's (0.02% (w/v) Ficoll, 0.02% (w/v) bovine serum albumin, 0.02% polyvinylpyrollodone), 15 olg/ml tRNA after hybndisation. The filters are washed sequentially in 5×SSC at 4° C., TAC (TAC is 3M tetramethyl ammonium chloride 50 mM (tris)[hydromethyl] aminomethane pH 8.0, 1 mM EDTA (ethylenediamione hetraceletic acid), 0.1% (w/v) sodium dodecyl sulphate) at 37° C. and finally in TAC at the desired temperature. This last wash determines the specificity. For AA1D, the temperature is 52.5° C. After exposure to x-ray film, only those clones which are completely complementary to AA1D are observed. Several of these clones are analyzed by DNA sequencing. All of them contain the first mutation but none of them contain the second (at cysteine 191) mutation.

To mutate the cysteine at position 191, a second oligonucleotide designated A1 is used. A1 has the following sequence:

5' GAG AGC AGC GCT GCC TTC TAG 3'

Figure 3A:
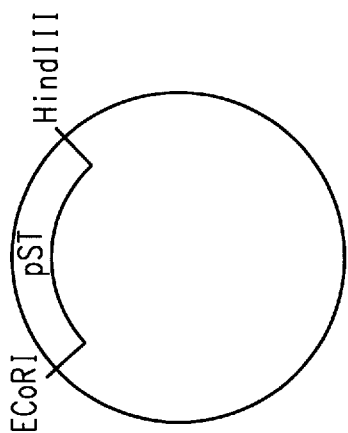
FIG. 3: DNA sequence analysis of M13mp11ST-single stranded DNA and M13mp11pST34-single stranded DNA using the Sanger dideoxy chain termination method. The order of the lanes from left to right is GATC for wild type porcine somatotropin (pST) followed by GATC for mutant pSTA34.
Figure 3B:
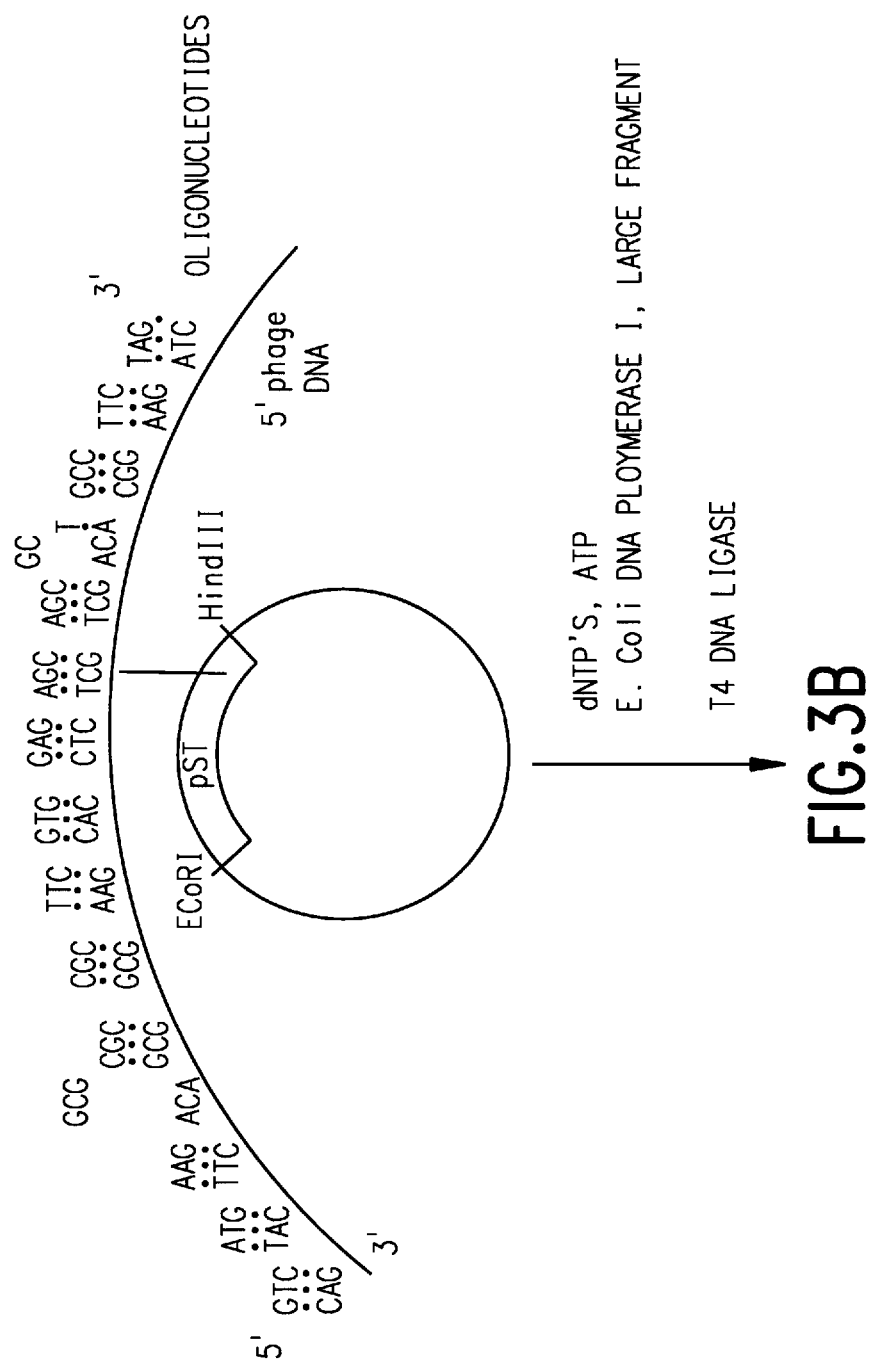
Figure 3C:
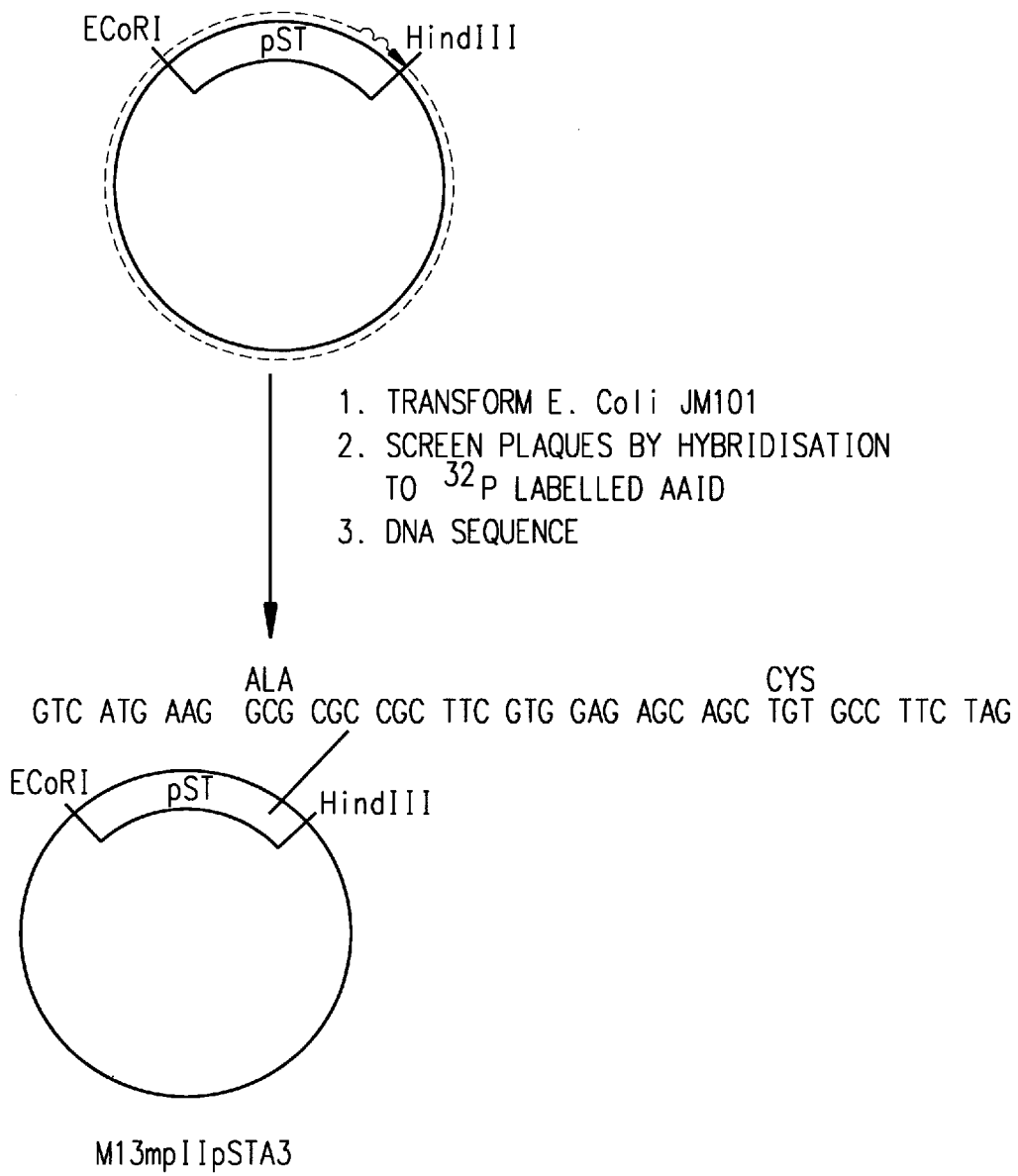

The process of mutagenesis is identical to that described above using AA1 except that the template DNA is M13mp11pSTA3 (this is the clone isolated from the AA1 mutagenesis which has the cysteine at position 183 converted to alanine) and the hybridisation is with A1. The final wash temperature is 56° C. DNA sequencing reveals that the identified clones have the expected sequence. The mutated clone is designated M13mp11pSTA34. The DNA sequence is illustrated in FIG. 3.

Figure 4:
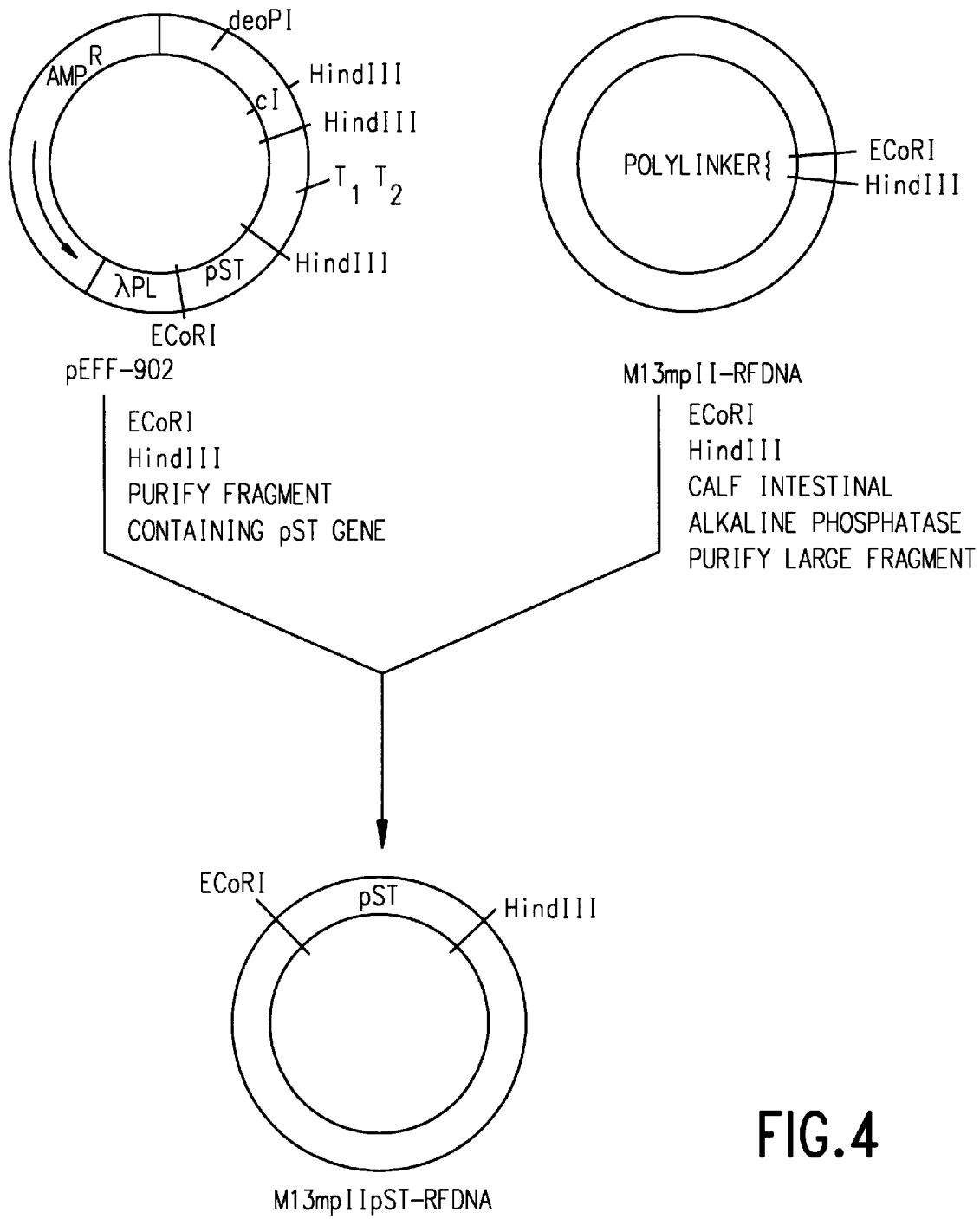
FIG. 4: Schematic representation of the mutagenesis schemes using oligonucleotides GLU3 and GLU4 and M13mp11pST-single stranded DNA.

In the second method, substitution of the small loop disulphide band is obtained by using two oligonucleotides in the same reaction and is diagrammed in FIG. 4. The two oligonucleotides have the following sequence:

```
5' GTC ATG AAG GAA CGC CGC TTC 3' GLU3
                GLU

5' GAG AGC AGC GAG GCC TTC TAG 3' GLU4
                GLU
```

The template single stranded DNA is M13 mp11pST. The two oligonucleotides and the template DNA, in the same reaction, are annealed, extended and ligated as before. The mixture is transformed into E. coli JM101. The difference in this method is that two lifts are taken from each plate. Each lift is hybridized separately to either $^{32}$P labeled GLU3 or GLU4. The final wash temperature for each oligonucleotide is 56° C. Only those plaques which are positive for both oligonucleotides are picked. DNA sequencing reveals that both Cys 183 and Cys 191 are converted to glutamic acid. The clone is designated M13mp11pSTE34 (ATCC Accession Number 40482). This method is used to obtain mutations preventing formation of the large loop disulphide by using two appropriate oligonucleotides as described above and M13mp11pST. Clearly by using M13mp11pSTA34 as the template DNA and two oligonucleotides appropriate for altering Cys 55 and Cys 166 to alanine, a clone is obtained in which all of the cysteine residues are converted to alanine.

The altered (mutant) clones are then reconstructed into the bacterial expression plasmid pRO211 (ATCC Accession Number 40483) as diagrammed in FIG. 5 (described in EP 173,280). The M13 clones are cut with EcoRI and HindIII and the pST gene fragment isolated. pRO211 is digested with the same enzymes treated with calf intestinal alkaline phosphatase and the large fragment isolated. The two pieces are ligated together with T4 DNA ligase and transformed into an appropriate bacterial strain, e.g. E. coli N99cI. In this strain a wild type k repressor is present. This prevents expression from the $P_L$ promoter in pRo211. Once the appropriate construction is isolated, it is then transferred into bacterial strains which contain a temperature sensitive k repressor, e.g. (ATCC Accession Number 67766) E. coli 4200. In these strains, the expression of pST is dependent on temperature. At 42° C., the repressor is inactive and expression occurs. At this stage, pST is prepared by procedures contained in EP 173,280 wherein expression occurs (incorporated herein by reference thereto). Expression of pST is not limited to these particular E. Coli strains. Other strains with appropriate properties are substituted. The plasmid expression vectors are deposited with the ATCC. The bacterial strains are deposited separately.

Other amino acid substitutions are made by the above procedures utilizing the appropriate codons and oligonucleotides. Similarly, these procedures are employed to modify a variety of animal somatotropins.

Among the modified recombinant animal somatotropins readily prepared by the above procedures are (Ala 55,166) rpST; (Ser 55,166)rpST; (Ala 183,191)rpST; (Glu 183,191) rpST; (Glu 183-Ala 191)rpST; (Ser 183,191)rpST; and (Glu 183-Ser 191)rpST.

Derivatized Animal Somatotropins

Derivatized animal somatotropins, recombinant preferred, are prepared by dissolution or dispersion of an animal somatotropin in water or an aqueous solution of guanidine hydrochloride, sodium bicarbonate or the like, which is adjusted to pH 8.4 with aqueous base such as sodium or ammonium hydroxide. To this solution is then slowly added dithiotheritol, i.e. (DL-threo-1, 4-dimercapto-2,3-butanediol). The addition is generally conducted under an atmosphere of nitrogen at room temperature. To the resulting solution is then added iodoacetamide, iodoacetic acid, sodium tetrathionate, methyl methanethiosulfonate, 1,3-propane sulfone or other derivatizing agent. The mixture is stirred for about one to four hours, then desalted by ultrafiltration. The solution is concentrated and then subjected to several cycles of redilution with water, aqueous guanidine hydrochloride or the like, followed by ultrafiltration. The residue from the final filtration is then lyophilized to yield the derivatized rpST.

METHOD OF USE

Advantageously, the novel animal somatotropins of the present invention are useful for improving the growth rate of animals, especially meat producing animal, and increasing the efficiency of feed utilization thereby. These compounds are also effective for enhancing the carcass quality of said animals, i.e. increasing the lean meat to fat ratio of said animals. Moreover, the compounds of the present invention are effective for increasing milk production in lactating animals and improving wool production in sheep and other animals raised for coats.

While the modified (substituted) or derivatized somatotropins of this invention are effective for treatment of animals to achieve the biological improvements described above, it appears that the improved effectiveness and usefulness of the modified or derivatized animal somatotropins of the invention is attributed, in part, to the inhibition of aggregation of the somatotropin produced by the modification or derivatization of said somatotropins. Such inhibition permits the preparation of markedly improved sustained release delivery systems which are not readily or effectively achieved with native somatotropins or recombinant somatotropins which are not modified or derivatized as described by the present invention.

It is also found that the modified or derivatized somatotropins of the present invention are highly stable and essentially free of aggregation due to dimer formation. Moreover, the modified or derivatized somatotropins of the invention lend themselves to use in the preparation of significantly improved sustained release compositions.

Where native animal somatotropins have been found to aggregate in a single day, parenteral compositions containing the modified or derivatized somatotropins of this invention continue to release the modified or derivatized somatotropin for 10 days or more.

Compositions

In practice, the compositions of the present invention are generally administered to the animals by injection in the form of biologically active parenteral compositions. Among the parenteral compositions useful for administration of the recombinant animal somatotropins of this invention are gels, pastes, microspheres, microcapsules, implants and the like. As such, there is considerable interest in providing dosage forms of biologically active substances which release the substance in a controlled manner and thus, reduce the frequency of administration.

The development of sustained release compositions of biologically active macromolecules presents special problems due to their complex modes of action and intricate structures of the macromolecules. Thus, the development of effective sustained release compositions that contain the biologically active somatotropin is required.

The compositions useful for this type of administration are prepared by dissolving the modified or derivatized animal somatotropin in dilute ammonium hydroxide and then adding a solution of an alkali metal benzoate, laurate, carbonate or the like thereto. A nonionic surfactant is thereafter admixed with the solution and the resulting mixture spray dried. The thus formed solids are then admixed with molten fat or wax or a mixture thereof and the resulting molten mixture sprayed through an air/liquid spray nozzle equipped with a heated jacket to maintain the incoming air and the molten phase at a temperature above the melting point. The microspheres are formed as the molten droplets cool. These are collected on a series of sieves in the desired size range of about 45 to 180 microns and retained for use. Microspheres which are not of the desired size range are recycled. Alternatively, the homogeneous mixture is fed onto a centrifugal disc and the microspheres thus formed collected as above, or the molten mixture are cooled and milled to the desired average particle size range.

The biologically active microspheres are then dispersed in a pharmaceutically and pharmacologically acceptable liquid vehicle for injection into the animal. The microsphere-liquid composition is generally administered by subcutaneous injection under the skin of the animal usually in the vicinity of the head, neck or ears.

The modified or derivatized animal somatotropins of the present invention also are prepared as biocompatible implants which are injected under the skin of the animal using a conventional pellet implant gun. These compositions are prepared by admixing a powdered modified or derivatized somatotropin with a wax such as castor wax or with a mixture of a copoly (glycolide/lactide), magnesium hydroxide, and a condensate of ethylene oxide prepared with a hydrophobic base formed by condensation of propylene oxide with propylene glycol. The thus formed compositions are then introduced into a pelleting press and formed into cylindrical pellets about ⅛ inch in diameter. The thus formed pellets are administered with a conventional pellet implant gun.

The present invention is further illustrated by the examples set forth hereinbelow.

EXAMPLE 1

Substitutions of the cysteines in the small loop disulphide bond using a long synthetic oligonucleotide.

An oligonucleotide designated AA1 has the following sequence:

5' GTC ATG AAG GCG CGC CGC TTG GTG GAG AGC AGC GCT GCC TTC TAG 3'

This alters the sequence of the rpST gene such that the codon for cysteine at position 183 is converted from TGT to GCG which codes for alanine and the cysteine at position 191 is converted from TGT to GCT which also codes for alanine. Therefore, the cysteines in the small loop are both converted to alanine. Single stranded M13mp11pST DNA is prepared from purified phage by standard protocols. 1000 ng of single stranded M13mp11pST DNA is mixed with 50 ng of AA1 oligonucleotide, which has previously been 5' phosphorylated with adenosine 5' triphosphate and polynucleotide kinase in a final volume of 1011 containing 1× annealing buffer (1× annealing buffer is 75 mMKcl 5 mMtrs pH8.0). The mixture is heated at 65° C. for 7 minutes and then kept at room temperature for 10 minutes. This protocol anneals the oligonucleotide to the single stranded DNA. The annealed DNA is then converted to a double stranded covalently closed form by the addition of 20 ll $H_2O$, 4 ll 10× fillin buffer, (1× fillin buffer is 27 5 mMgCl$_2$ pH7.5 2 mM DTT) 1 ll 20 mM ATP, 2 ll dNTP's (a mixture of the four deoxyribonucleotide 5' triphosphates each at a concentration of 2 mM), 2U T4 DNA ligase and 2U DNA polymerase I large fragment (for unit definition see New England Biolabs catalogue, 1986). The mixture is incubated for 1 hour at room temperature. The mixture is then transformed into E. coli JM101 by a standard calcium chloride procedure. After overnight incubation at 37° C. plaques can be seen on a lawn of JM101. The plaques are lifted onto nitrocellulose filters and processed for hybridisation by standard protocols. A second oligonucleotide designated AA1D is used for detection of the mutants. AA1D has the following sequence 5' C ATG AAG GCG CGC CGC TT 3'. It is radioactively labelled at the 5' end with d-32P-ATP and polynucleotide kinase. Hybridisation is overnight at 37° C. in 5×SSC, 1× Denhardt's, 15 olg/ml tRNA. The filters are washed sequentially in 5×SSC at 4° C., TAC at 37° C. and finally in TAC at the desired temperature. This last wash determines the specificity. For AA1D, the temperature is 52.5° C. After exposure to x-ray film only those clones which are completely complementary to AA1D are observed. Several of these clones are analyzed by DNA sequencing. All of them contain the first mutation but none of them contain the second (at cysteine 191) mutation. To mutate the cysteine at positions 191, a second oligonucleotide designated A1 is used. A1 has the following sequence:

5' GAG AGC AGC GCT GCC TTC TAG 3'

The process of mutagenesis is identical to that described in Example 1 above using AA1 except that the template is M13mp11pSTA3 (this is the clone isolated from the AA1 mutagenesis which has the cysteine at position 183 converted to alanine) and the hybridisation is with A1. The final wash temperature is 62° C. DNA sequencing reveals that the identified clones have the expected sequence. The mutated clone is designated M13mp11pSTA34.

EXAMPLE 2

Substitution of the cysteines in the small loop of recombinant porcine somatotropin Substitution of the small loop disulphide band is obtained by using two oligonucleotides in the same reaction. The two oligonucleotides have the following sequence:

5' GTC ATG AAG GAA CGC CGC TTC 3' GLU3
                               GLU

5' GAG AGC AGC GAG GCC TTC TAG 3' GLU4
                               GLU

The template single stranded DNA is M13mp11pST. The two oligonucleotides and the template DNA, in the same reaction, are annealed, extended and ligated as before. The mixture is transformed into E. coli JM101. The difference in this method is that two lifts are taken from each plate. Each lift is hybridized separately to either $^{32}$p labeled GLU3 and GLU4. The final wash temperature for each oligonucleotide is 56° C. Only those plaques which are positive for both oligonucleotides are picked. DNA sequencing reveals that both Cys 183 and Cys 191 are converted to glutamic acid. This method is used to obtain mutations preventing formation of the large loop disulphide by using two appropriate oligonucleotides as described above and M13mp11pST. Clearly by using M13mp11pSTA34 as the template DNA and two oligonucleotides appropriate for altering Cys 55 and Cys 166 to alanine, a clone is obtained in which all of the cysteine residues are converted to alanine.

EXAMPLE 3

Reconstruction into bacterial expression plasmids

The altered (mutant) clones are reconstructed into the bacterial expression plasmid pRO211 (described in EP 173280)incorporated herein by reference thereto. The M13 clones are cut with ECoRI and HindIII and the pST gene fragment isolated. pRO211 is cloned with the same enzymes treated with calf intestinal alkaline phosphatase and the large fragment isolated. The two pieces are ligated together with T4 DNA ligase and transformed into an appropriate bacterial strain, e.g. N99cI$^+$. In this strain a wild type k repressor is present. This prevents expression from the $P_2$ promoter in pRO211. Once the appropriate construction has been isolated, it is then transferred into bacterial strains which contain a temperature sensitive k repressor, e.g. 4200. In these strains, the expression of rpST is dependent on temperature. At 42° C., the repressor is inactive and expression occurs. At this stage, rpST can be prepared by procedures contained in EP 173280, incorporated herein by reference thereto. The E. coli strain which are used for expression of the pST gene product are not limited to E. coli 4200. Any appropriate E. coli strain can be utilized.

Following the procedures of Examples 1, 2 and 3 above, but substituting the appropriate codons for alanine, serine, glutamic acid, arginine, trypophan, or asparagine for cysteine at positions 183 and 191 converts TGT for cysteine to TCN, AGC or AGT for serine, GAG, or GAA for glutamic acid, CGN, AGA or AGG for arginine, AAT or AAC for asparagine, GCN for alanine, or TGG for tryptophan at said position.

EXAMPLE 4

Preparation of (Cam-Cys 55, 166, 183, 191)rPST

A solution of 100 mg recombinant porcine somatotropin (rpST) and 33 mL of 7M guanidine HCl is prepared and the pH adjusted to 8.4 with NaOH. To this solution is added 18 mg (20 equivalents) of dithiothreitol and the reaction mixture stirred for one hour at room temperature under a $N_2$ atmosphere. To this solution is then added 84 mg (100 equivalents) of iodoacetamide and the reaction mixture is stirred at room temperature for four hours. The reaction mixture is diluted with 35 mL of $H_2O$ and guanidine HCl and excess reagents are removed by ultrafiltration through an Amicon UM2 membrane (molecular weight cut off approximately 1000 Daltons) in a Amicon Model 8400 stirred cell. After several cycles of redilution and refiltration, the residual aqueous solution is lyophilized to constant weight to yield approximately 100 mg of fluffy white solid. The electrophoretic mobility of the product on SDS-PAGE gel under non-reducing conditions is different from rpST. The product is the derivatized recombinant porcine somatotropin indicated hereinabove.

EXAMPLE 5

Preparation of (Cam-Cys 183,191)rpST

To a solution of degassed 0.02M NaCl (225 ml) is added 3.375 gm of recombinant porcine somatotropin (rpST) and the pH adjusted to 8.1 with dilute HCl, while maintaining the pH of this solution at 8.1 15 mg/ml, 0.9463 gm of dithiothreitol dissolved in 31.5 ml, water is added to the rpST solution. The mixture is permitted to stand at room temperature for one hour and then the pH is raised to 8.4. 5.7 gm of iodoace-tamide dissolved in 40.5 ml of water is then added dropwise to the rpST solution while maintaining the pH at 8.4. Formation of a fine precipitate occurs during this addition which is removed by centrifugation. The clear supernatant liquid is removed and passed through a Sephadex G-25 column to remove excess low molecular weight materials. The high molecular weight rpST fraction 342.8 gm is collected and freeze dried to give 2.2 gm of (Cam-Cys 183, 191)rpST.

EXAMPLE 6

Preparation of (Cm-Cys 183,191)rpST

To a solution of 200 mg of recombinant porcine somatotropin (rpST) and 100 ml of 0.5N NaHCO$_3$ (pH adjusted to approximately 8.4 with aqueous ammonium hydroxide) is added 15 mg of dithiothreitol and the reaction mixture allowed to stir at room temperature for one hour. 50 Mg of iodoacetic acid is added and the reaction mixture stirred at room temperature for two hours. The reaction mixture is then desalted by ultrafiltration through an Amicon UM2 membrane in a Amicon Model 8400 stirred cell. After several cycles of redilution and refiltration the residual solution is lyophelized to constant weight. Approximately 200 mg of fluffy white solid is recovered. The product obtained is the derivatized recombinant porcine somatotropin as indicated herein.

Following the above procedure but substituting recombinant bovine somatotropin, recombinant ovine somatotropin, recombinant horse somatotropin, recombinant human or recombinant avian somatotropin for recombinant porcine somatotropin gives respectively:
1) (Cm-Cys 183,191)rbST
2) (Cm-Cys 183,191)roST
3) (Cm-Cys 183,191)rhoST
4) (Cm-Cys 184,191)rhST
5) (Cm-Cys 183,191)raST

EXAMPLE 7

Preparation of ($^-O_3$S-Cys 55,166,183,191)rpST

A solution of 200 mg recombinant porcine somatotropin (rpST) and 50 mL of 7N guanidine HCl is prepared and the pH adjusted to approximately 8.4 with sodium hydroxide. To this solution is added 33 mg of dithiothreitol and the reaction mixture stirred at room temperature for one hour. To this solution is added 200 mg of sodium tetrathionate. The pH immediately drops to ca. 6 and this is adjusted back to 8.4 with NaOH. The mixture is then allowed to stir for 2 hours. The solution is ultrafiltered through an Amicon UM2 membrane. The reaction mixture is concentrated to approximately 20 mL and then rediluted with about 40 mL of 3N guanidine HCl and refiltered. After concentration to ca. 20 mL of the solution is diluted with $H_2O$ and reconcentrated. This process is repeated two additional times and the residue is lyophilized to constant weight. Approximately 200 mg of white solid product is obtained. The product is the derivatized recombinant porcine somatotropin described hereinabove.

EXAMPLE 8

Preparation of ($^-O_3$S-Cys 183,191)rpST

To a solution of 250 mg of recombinant porcine somatotropin (rpST) in 100 mL of $H_2O$ (pH adjusted to approximately 8.4 with NaOH) is added 70 mg of dithiothreitol. The solution is stirred for one hour at room temperature. To the solution of reduced rpST is added 400 mg of sodium tetrathionate and the solution is stirred at room temperature for four hours. The reaction mixture is filtered through a Amicon UM2 membrane, and concentrated to about 20 mL. This is diluted with about 200 mL of $H_2O$ and reconcentrated. This procedure is repeated two more times. The final solution lyophilized to constant weight yielding about 240 mg of white powder. This is the derivatized recombinant porcine somatotropin described hereinabove.

EXAMPLE 9

Preparation of (MeS-Cys 183,191)rpST 200 mg of recombinant porcine somatotropin (rpST) are dissolved in 100 mL of $H_2O$. The pH of this solution is adjusted to ca. 8.4 with aqueous NaOH). To this solution is added 15 mg of dithiothreitol (DTT) and the reaction is stirred at room temperature for one hour. After the reduction is completed 24 ll of methyl methanethiosulfonate is added and the reaction mixture stirred at room temperature for four hours. During the reaction the pH is maintained at 8.4 by addition of 1% NaOH as required. The solution is ultrafiltered through a UM2 membrane and concentrated to about 20 mL. The residue is diluted with 200 mL of $H_2O$ and reconcentrated. The solution then is lyophilized to yield 210 mg of product described above, i.e. the derivatized recombinant porcine somatotropin described hereinabove.

Following the above procedure but substituting recombinant bovine somatotropin, recombinant ovine somatotropin, recombinant horse somatotropin, recombinant human somatotropin or recombinant avian somatotropin for recombinant porcine somatotropin gives the following products:
1) (MeS-Cys 183,191) recombinant bovine somatotropin
2) (MeS-Cys 183,191) recombinant ovine somatotropin
3) (MeS-Cys 183,191) recombinant horse somatotropin
4) (MeS-Cys 184,191) recombinant human somatotropin
5) (MeS-Cys 183,191) recombinant avian somatotropin

EXAMPLE 10

Preparation of ($HO_3SCH_2CH_2CH_2$-Cys 183,191)-rpST

To a solution of 200 mg of recombinant porcine somatotropin (rpST) in 100 mL of $H_2O$ adjusted to pH=8.4 is added 15 mg of dithiothreitol, and the reaction mixture stirred at room temperature for one hour under an $N_2$ atmosphere. To this solution is added 50 mg of 1,3-propane sulfone and the solution stirred at room temperature for six hours. The pH is maintained at 8.4 by addition of 1% NaOH. The crude product is concentrated by ultrafiltration through a UM2 membrane to ca. 20 mL. This is twice diluted to 200 mL and reconcentrated. The final solution is lyophilized to yield 200 mg of the white solid product described above, i.e. the derivatized recombinant porcine somatotropin.

Advantageously, substitution of the appropriate recombinant animal somatotropin for recombinant porcine somatotropin for the above procedure produces the following somatotropins.
1) ($HO_3SCH_2CH_2CH_2$-Cys 183,191) recombinant bovine somatotropin
2) ($HO_3SCH_2CH_2CH_2$-Cys 183,191) recombinant ovine somatotropin
3) ($HO_3SCH_2CH_2CH_2$-Cys 183,191) recombinant horse somatotropin
4) ($HO_3SCH_2CH_2CH_2$-Cys 184,191) recombinant human somatotropin
5) ($HO_3SCH_2CH_2CH_2$-Cys 183,191) recombinant avian somatotropin

EXAMPLE 11

Stability profiles of modified or derivatized recombinant animal somatotropins

A concentrated solution of the recombinant animal somatotropin derivative (up to 100 mg/ml) in phosphate buffered saline pH 7.4 ($NaH_2PO_4$ $H_2O$ 0 3.45 gm, $Na_2HPO_4$ 3.55 gm, NaCl 9.50 gm dissolved in distilled water to 1000 ml) is prepared. This is filtered through a millipore sterile Millex-0.22 um filter unit and 0.1 ml aliquots placed into tubes. These are placed in a 45° C. oven and removed at the required intervals. The contents are then diluted with phosphate buffered saline. The supernatent is assayed for monomer and dimer content by HPLC. A mass balance is done, any precipitated material is recorded. Results are compared with the initial concentrations, and a stability profile documented.

Alternately, a somatotropin derivative exhibiting poor solubility at pH 7.4 is dissolved at a less preferred pH (4–10) or is evaluated as a suspension.

| Sample | 2 days Fraction Soln. (Dimer) | 5 days Fraction Soln. (Dimer) | 6 days Fraction Soln. (Dimer) | 7 days Fraction Soln. (Dimer) |
|---|---|---|---|---|
| rpST Tech. | 93.1(17.2) | 92.4(27.6) | 92.0(34.9) | *85.9(29.4) 89.5(31.0) |
| rpST Tech. | — | 79.8(20.7) | — | — |
| rpST Tech. | — | 81.5(18.6) | — | — |
| (Cam-Cys 183–191)rpST | — | 75.2(2.0) | — | — |
| (Cam-Cys 183, 191)rpST | — | 72.8(1.0) | — | — |
| (Cam-Cys 183, 191)rpST | — | — | 57.8(2.0) | — |
| (Cam-Cys 183, 191)rpST | — | — | — | 73.0(3.0) |
| (Mes-Cys 183, 191)rpST | 79.7(2.2) | — | — | 73.4(3.9) |
| Disulfite rpST | 83.2(1.0) | — | — | *73.9(1.5) 85.0(1.6) |

| Description | Soluble Fraction (Dimer) | |
|---|---|---|
| | 2 days | 7 days |
| Carboxymethyl deriv. of rpST | 92.8(5.3) | 85.6(5.9) |
| Methyl sulfide deriv. of rpST | 77.6(2.4) | 63.5(3.0) |
| Hydroxysuccinic acid deriv. of rpST | 91.5(7.8) | 69.9(5.6) |
| Carbamidomethylated (CAM) deriv. of rpST | 78.0(1.0) | 57.4(1.0) |
| rpST Technical batch | 89.5(16.6) | 75.5(30.9) |

*Extracted into PBS buffer. Rest all extracted into CBS.

EXAMPLE 12

Preparation of injectable microspheres for the parenteral administration of recombinant animal somatotropin derivatives Preparation of the novel recombinant animal somatotropins in a size range suitable for incorporation in microspheres by spray drying is accomplished by dissolving the recombinant animal somatotropin derivative in dilute ammonium hydroxide solution and then adding desired salt solutions such as sodium benzoate. A nonionic surfactant such as a block copolymer of ethylene oxide and propylene oxide is added and allowed to dissolve with constant gentle mixing. The solution is then spray-dried. A Buchi mini spray dryer, model #190 maybe used for this purpose.

A homogeneous mixture of the thus prepared active ingredient and additives in the molten fat, wax or mixture thereof is prepared and the resulting mixture sprayed through an air/liquid spray nozzle equipped with a heated jacket to maintain the incoming air and the molten phase at a temperature above the melting point. The microspheres are formed as the molten droplets cool and are collected on a series of sieves in the desired size range of about 45 to 180 microns and retained for use. Microspheres which are not of the desired size range are collected for recycling. Alternatively, the homogeneous mixture are fed onto a centrifugal disc and the microspheres thus formed are collected as above, or the molten mixtures are cooled and milled to the desired average particle size range.

Waxes and fats which are suitable for use in the compositions of this invention in general have melting points higher than 40° C. *These waxes are defined as a low-melting organic mixture or compound of high molecular weight, solid at room temperature and generally similar in composition to fats and oils except that it contains no glycerides. Some are hydrocarbons; others are esters of fatty acids and alcohols. They are classed among the lipids. Waxes are thermoplastic, but since they are not high polymers, they are not considered in the family of plastics. Common properties are water repellency; smooth texture; nontoxicity; freedom from objectionable odor and color. They are combustible, and have good dielectric properties. Soluble in most organic solvents; insoluble in water. The major types are as follows:

* The Condensed Chemical Dictionary Tenth Edition Pg. 1094 Van Nostrand Reinhold Publisher I. Natural
1. Animal (beeswax, lanolin, shellac wax, Chinese insect wax).
2. Vegetable (carnauba, candelilla, bayberry, sugar cane)
3. Mineral
   (a) Fossil or earth waxes (ozocerite, ceresin, montan)
   (b) petroleum waxes (paraffin, microcrystal-line) (slack or scale wax)

II. Synethetic
1. Ethylenic polymers and polyol ether-esters ("Carbowax," sorbitol)
2. Chlorinated naphthalenes ("Halowax")
3. Hydrocarbon type via Ficher-Tropsch synthesis The fat of the invention may be defined as a glyceryl ester of higher fatty acids such as stearic and palmitic. Such esters and their mixtures are solids at room temperatures and exhibit crystalline structure. Lard and tallow are examples. There is no chemical difference between a fat and an oil, the only distinction being that fats are solid at room temperature and oils are liquid. The term "fat" usually refers to triglycerides specifically, whereas "lipid" is all-inclusive.

The fat is preferably long chain $C_{10}$–$C_{24}$ fatty acid, alcohol, ester, salt, ether or mixture thereof, with mono-, di-, or triglycerides composed predominantly of stearates, palmitates, laurates, linoleates, linolenates, oleates, and residues or mixtures thereof, having melting points greater than 50° C. being most preferred. Glycerol tristearate is a most preferred fat. Additionally, lipophilic salts of fatty acids such as magnesium stearate and the like are also suitable.

The microspheres of the invention are dispersed in a pharmaceutically and pharmacologically acceptable liquid to obtain a slow release composition for parenteral administration. The vehicle is aqueous buffered systems or oil systems. The oil is a vegetable or an animal oil. A preferred oil is a neutral triglyceride liquid fat. A neutral oil is one containing no residual acid. Vehicles suitable for use in the compositions of this invention include aqueous systems such as buffered salines; organic solvents such as glycols and alcohols; and water immiscible liquids such as oils, depending upon the solubility of the active ingredient being administered. Data obtained are reported in Table I.

TABLE II

Microsphere formulations of recombinant animal somatotropin

| | | Core | | | Coating | | | |
|---|---|---|---|---|---|---|---|---|
| recombinant animal % somatotropin derivative | % cholic acid | % deoxycholic acid | % cholesterol | % cholesterol | % glyceryl tristearate | % PVP | % beeswax | % phosphatidylcholine |
| 50 | 50 | — | — | 42.5 | 42.5 | 5 | — | — |
| 20 | 80 | — | — | 42.5 | 42.5 | 5 | — | — |
| 75 | 25 | — | — | 42.5 | 42.5 | 5 | — | — |
| 50 | — | 50 | — | 40 | — | 5 | 40 | 5 |
| 20 | — | 80 | — | 40 | — | 5 | 40 | 5 |
| 75 | — | 25 | — | 40 | — | 5 | 40 | 5 |
| 50 | — | — | 50 | 42.5 | 42.5 | 5 | — | — |
| 20 | — | — | 20 | 42.5 | 42.5 | 5 | — | — |
| 75 | — | — | 75 | 42.5 | 42.5 | 5 | — | — |

TABLE I

Microsphere Compositions

| Composition # | Matrix | rPST Derivatives | Additives (%) Buffer/Pres. | Additives (%) Surfactant |
|---|---|---|---|---|
| 1 | GMS | 2.5 | — | — |
| 2 | | 20 | — | — |
| 3 | GMS/soya oil | 30 | — | — |
| 4 | GDS | 10 | — | — |
| 5 | | 10 | NaLaurate (1.4) | — |
| 6 | | 25 | NaBenzoate (1.6) | Surf. B (0.12) |
| 7 | | 25 | NaCarb/bicarb (1.3) | Surf. A (0.18) |
| 8 | GTS/GDS (19:1) | 15 | — | — |
| 9 | | 10 | NaBenzoate (0.6) | Surf. B (0.05) |
| 10 | GTS/GDS (9:1) | 10 | — | Surf. B (0.1) |
| 11 | GTS/beeswax (9:1) | 7.5 | — | — |
| 12 | GTS/GMS (19:1) | 15 | NaBenzoate (1.4) | — |
| 13 | GTS/Soya oil (19:1) | 7.5 | — | — |
| 14 | GMS/Carnauba (1:2) | 20 | — | — |
| 15 | | 10 | NaBenzoate (0.8) | — |
| 16 | | 10 | — | Surf. B (0.05) |
| 17 | | 25 | NaBenzoate (0.75) | Surf. B (0.12) |
| 18 | | 25 | NaBenzoate (3.2) | Surf B (0.12) |
| 19 | | 25 | — | Surf. B (0.12) |
| 20 | | 25 | — | Surf. A (0.48) |
| 21 | | 25 | NaCarb/bicarb (1.2) | — |
| 22 | GTL | 33 | NaBenzoate (2.1) | Surf. A (0.17) |
| 23 | GTS/GDS (12:1) | 15 | CaBenzoate (1.1) | — |
| 24 | Beeswax/Soya Oil (2:1) | 30 | — | — |
| 25 | GTS | 7.5 | — | — |
| 26 | GMS/Soya Oil (47.25/24) | 25 | — | Sorbitan |
| 27 | | 15 | — | monoleate (3.75) |
| 28 | GMS | 10 | — | POE (23) stearate (9.0) |
| 29 | GMS | 20 | | PEG 6000 (9.0) |
| 30 | GMS | 20 | — | PEG 6000 (4.0) |
| 31 | GMS | 20 | — | PEG 6000 (0.8) |
| 32 | GMS | 20 | — | PEG 400 distearate (8.0) |
| 33 | GMS | 20 | — | PEG 400 distearate (1.57) |
| 34 | GMS | 20 | — | PEG 1540 distearate (16.0) |
| 35 | Diethylene glycol monostearate | 25 | — | — |

EXAMPLE 13

Bile Acid Microspheres

A buffered solution of rpST derivative and bile acid is spray dried in a Buchi Model 190 spray dryer. This fine particle powder (10 parts) is suspended in a methylene chloride solution of coating materials (1 part). This suspension is spray dried. The coated microspheres are suspended in a suitable suspending vehicle prior to injection. These compositions are described in Table II. Other derivatized or modified recombinant animal somatotropins of the present invention, including the modified recombinant porcine, bovine, ovine, horse, human and avian somatotropins, wherein the cysteines in the small loop at the 183 and 191 positions (184 and 191 for humans) of the recombinant animal somatotrophins are replaced by alanine, serine, glutamic acid, arginine, lysine or the like, are prepared as microspheres in accordance with the description in Table II.

EXAMPLE 14

Preparation of recombinant animal somatotropin implants

Implants are prepared by weighing a sufficient quantity of the ground homogeneous mixture of the desired recombinant animal somatotropin derivative and the desired diluents. This mixture is then compressed on a carver press at from 1000 to 5000 psig in a 3⁄16" or 1⁄8" diameter cylindrical die or on a rotary tablet press using the required punch and die. The implants thus prepared are then coated with either biodegradable or nonbiodegradable coatings by procedures A and B.

PROCEDURE A

Non-Biodegradable Silicon Polymer

Clean grade silicon elastomer (10 parts) is mixed with curing agent (one part) on a watch glass with a spatula. This is deaerated in a dessicator for 30 minutes. The implants are grasped by the ends with tweezers, rolled into the silicon polymer, placed on end on aluminum foil and cured at 40° C. for five hours. One or both of the ends are removed with a razor blade leaving the "shaft" of the cylinder coated.

Alternatively, implants are dip coated with 20% to 40% of a medical adhesive, sold under the trademark SILASTIC, by Dow Corning, which has been dispersed in hexane, and dried and cured at 40° C. to 50° C. overnight before removing the coating from one or both of the base ends.

PROCEDURE B

Biodegradable Coatings

The polymer or copolymer (one part) is dissolved in chloroform (three to eight parts). Each implant is grasped by the ends with tweezers, dipped into the polymer solution, and then the chloroform evaporated at room temperature. Each implant is coated twice. After the coating dried overnight at room temperature, the polymer ends are removed with a razor blade, leaving the long cylindrical "shaft" coated.

| Implant formulation | | | |
|---|---|---|---|
| % recombinant porcine somatotropin derivative | % Magnesium stearate | % ethyl cellulose | % Castor Wax |
| 50 | — | 5.0 | 45 |
| 40 | — | 5.0 | 50 |
| 20 | — | 5.0 | 75 |
| 50 | 0.5 | 3.5 | 46 |
| 20 | 0.5 | 3.5 | 76 |

| % rpST derivative | % cholesterol | % surfactant | % glyceryl tristearate |
|---|---|---|---|
| 30 | 68 | 2 | — |
| 15 | 41.5 | 2 | 41.5 |

| % rpST derivative | % stearic acid |
|---|---|
| 50 | 50 |
| 20 | 80 |

Alternatively, rpST or other recombinant animal somatotropins is blended with surfactants, buffer salts, and/or preservatives in an aqueous solution. This solution is then spray-dried in a Buchi Model 190 spray dryer giving a small particle size powder. This powder is then melt-blended with a fat or wax and molded into cylindrical implants. The implants prepared above are then coated with either a biodegradable or a non-degradable polymer using procedure A or B.

| Implant Formulations | | | |
|---|---|---|---|
| % rpST derivative | % glyceryl tristearate | % sodium benzoate | % surfactant |
| 28 | 69.9 | 2.0 | 0.15 |
| 15 | 82.9 | 2.0 | 0.15 |
| 50 | 48.5 | 1.5 | 0 |

EXAMPLE 15

Preparation of implants using (Cam-Cys 183,191) rpST and evaluation of said implants by in vitro dissolution To 1.3 ml of $CH_2Cl_2$ is added 92.4 ms of co-poly (glycolide/lactide) copolymer, 5.3 mg of a nonionic block copolymer of propylene oxide and ethylene oxide marketed by BASF Wyandottee Corp. as pluronic 127 which has an average molecular weight of 12,500, m.p. 56 and Brookfield viscosity of 3100 (cps)$^{35}$, 5.3 mg of 200 mesh mg $(OH)_2$ and 74.6 mg of powdered (Cam-Cys 183,191)rpST. The mixture is agitated, poured over a large surface petri dish and the $CH_2Cl_2$ allowed to evaporate at room temperature and then dried by vacuum drying. The dried residue is collected and formed in ⅛" diameter cylindrical implants using a Carver Press at about 1000 psig. The thus formed implants weigh 60 to 70 mg each and are designated I-1.

A second set of implants are prepared by mixing together in a Vortex-genie mixer 128 mg of powdered castorwax (–270 mesh) and 32 mg of powdered (Cam-Cys 183,191) rpST. The thus prepared mixture is then formed into ⅛" diameter cylindrical implants in the manner described above. The pellets weigh 60 to 70 mg each and are designated I-2.

A third set of implants are also prepared by the procedures described above using 96 mg of –270 mesh castorwax and 64 mg of powdered (Cam-Cys 183,191)rPST. The ⅛" diameter cylindrical implants prepared as descried above weigh 60 to 70 mg and are designated I-3.

The thus prepared implants are then subjected to an in vitro dissolution evaluation. Each of the implants is placed in a separate plastic tube containing 10 ml of a phosphate buffer solution (ph 7.4 with 0.05% Na azide) and the tubes placed in a shaking water rack where the tubes are shaken while the temperature of the water in the unit is maintained at 39° C. The tubes are shaken for one day then the solutions removed from each tube and analyzed for rpST by HPLC and the solution discarded. New phosphate buffer solution is added to each tube and the tubes shaken for three additional days thereafter. The solutions from each tube is again analyzed for rpST by HPLC and the solution again discarded. New phosphate buffer is again added to each tube and the tube again shaken for three days then analyzed again for rpST.

The implants used in these determinations are described below along with the results obtained. The phosphate buffer solution is ($NaH_2PO_4 \cdot H_2O$ 0 3.45 g, $Na_2HPO_4$ 3.55 g, Nacl 9.5 g dissolved in distilled water to 1000 ml.

| Implant Preparation and Designation | | |
|---|---|---|
| Origin of Implant | Wt. of Implant | rpST in Implant (Theory) mg |
| I-1 | 69.6 mg | 29.23 mg |
| I-2 | 68.7 mg | 28.85 mg |
| I-3 | 62.8 mg | 12.56 mg |
| I-4 | 63.3 mg | 12.66 mg |
| I-5 | 66.8 mg | 26.72 mg |
| I-6 | 66.2 mg | 26.48 mg |

In Vitro Dissolution Results

| Vol of release media (ml) | Day | I-1 % Dimer | I-2 % Dimer | I-3 % Dimer | I-4 % Dimer | I-5 % Dimer | I-6 % Dimer |
|---|---|---|---|---|---|---|---|
| 10 | — | Start | Start | Start | Start | Start | Start |
| 10 | 1 | 1.59 (low) | 1.184 (1.3%) | 0.485 (low, not measured | 0.499 (low, not measured | 1.605 (low) | 1.570 (low) |
| 10 | 4 | 0.417 (low) | 0.459 (1.7%) | 0.063 (low) | 0.068 (low) | 0.136 (low) | 0.140 (low) |
| 10 | 7 | 0.044 (low, not measured | 0.038 (low, not measured | 0.007 (low, not measured | 0.007 (low not measured | 0.019 (low, not measured | 0.019 (low, not measured |

Cumulative Release of rPST

| Day | Cumulative mg. released | Cumulative % of orignal released |
|---|---|---|
| | I-1 plus I-2 | |
| 1 | 11.72 | 40.4% |
| 4 | 16.10 | 55.4% |
| 7 | 16.51 | 56.9% |
| | I-3 plus I-4 | |
| 1 | 4.92 | 39.02% |
| 4 | 5.58 | 44.25% |
| 7 | 5.65 | 44.81% |
| | I-5 plus I-6 | |
| 1 | 15.88 | 59.7 |
| 4 | 17.26 | 64.89% |
| 7 | 17.45 | 65.6% |

EXAMPLE 16

Preparation of microencapsulated recombinant animal somatotropin

Poly(lactide-co-glycolide), 0.85 g, is dissolved in 29.8 g of chloroform and vortexed for 2 minutes. A recombinant porcine somatotropin derivative (Cam-Cys 183,191)rpST, 0.150 g, which has been dry sieved thru a 25-micron stainless steel sieve, is then added to the polymer/chloroform solution and vortexed for 3 minutes. The resulting suspension of the protein is then charged to a 50-ml round bottom vessel filled with a mechanical stirrer. The stir speed is set at 700 rpm at ambient temperature. An additional 3.2 g of chloroform is used to rinse the initial vessel. Then, the total chloroform quantity is 32.95 g. Silicone oil (350 cs) is then added (13.1 g over a period of 8 minutes) to precipitate the poly(lactide- co-glycolide). The contents of the flask are transferred to 1720 g of heptane with mechnaical stirring in a 4-liter flask. After 3 hours, the hardened microspheres are filtered through a series of stainless-steel sieves and dried under vacuum.

Other polymers and solvents useful for microencopsulation of modified recombinant animal somatotropins wherein one or more of the cysteine, amino acid residues at the 55, 166, 183 or 191 positions of the recombinant animal is replaced by a different amino acid residue or a derivatized recombinant in which one or both of the sulfide bridges between the cysteines at the 55 and 166 positions or between the 183 and 191 positions is reduced and derivatized, are listed below.

Abbreviations used in the listing of materials set forth below are:

A=as polymerized sample
B=reprecipitated sample
gly=glycolide
lact=lactide
capro=caprolactone
TMC=trimethylene carbonate
PHB=polyhydroxybutyrate
PHV=polyhydroxyvalerate
PEO=polyethylene oxide Polymers useful for Microencapsulation of modified and derivatized recombinant animal somatotropin

| Polymer | Ninh (Solvent) | Compositions (Wgt. %) |
|---|---|---|
| Gly/dl-lactide | $0.36^A$ (HFIP) | $43.6/56.4^A$ |
| Gly/dl-lactide | $0.52^A$ (HFIP) | $42.4/57.4^A$ |
| Gly/dl-lactide | $0.63^B$ (HFIP) | $43.3/56.7^B$ |
| Gly/dl-lactide | $0.66^B$ (HFIP) | $41.2/58.8^B$ |
| Gly/dl-lactide | $0.61^A$ (HFIP) | $41.6/58.4^A$ |
| Gly/dl-lactide | $0.22^B$ (HFIP) | $41.5/58.5^B$ |
| Gly/dl-lactide | $0.26^B$ (HFIP) | $40.6/59.4^B$ |
| Gly/dl-lactide | $0.27^B$ (HFIP) | $40.7/59.3^B$ |
| Gly/L-lact | $0.2^B$ ($CHCl_3$) | $48/52^B$ |
| dl-lact | $0.46^B$ (HFIP) | $100^B$ |
| dl-lact | $0.27^B$ (HFIP) | $100^B$ |
| PHB | $2.92^A$ (HFAS) | $100^A$ |
| PHB/HV | $3.27^A$ (HFAS) | $70/30^A$ |
| Capro/l-lact | $0.45^A$ ($CHCl_3$) | $84.6/15.4^A$ |
| Capro/l-lact | $0.46^A$ ($CHCl_3$) | $84.0/16.0^A$ |
| Capro/l-lact | $0.51^A$ ($CHCl_3$) | $85.2/14.8^A$ |
| Capro/l-lact | $0.50^A$ ($CHCl_3$) | $84.4/15.6^A$ |
| Capro/l-lact | $0.39^A$ ($CHCl_3$) | $85.1/14.9^A$ |
| Capro/l-lact | $0.36^A$ ($CHCl_3$) | $86.1/13.9^A$ |
| Capro/l-lact | $0.31^B$ ($CHCl_3$) | $11.4/88.6^B$ |
| Capro/gly | $0.34^A$ ($CHCl_3$) | $84.0/16.0^A$ |
| gly/PEO 8,000/TMC | $0.33^B$ ($CHCl_3$) | $50.3/8.4/41.3^B$ |
| gly/PEO 8,000/TMC | $0.38^B$ ($CHCl_3$) | $58.2/4.8/37.0^B$ |
| gly/dl-lactide/ PEO 8,000 | $0.35^B$ ($CHCl_3$) | $35.8/54.4/9.8^B$ |
| l-lact/TMC | $0.26^B$ ($CHCl_3$) | $85.4/14.6^B$ |
| | $0.23^B$ ($CHCl_3$) | $69/31^B$ |

$^A$= as polymerized sample
$^B$= reprecipitated sample

EXAMPLE 17

Hypox rat test method for determining the growth enhancement of animals receiving modified or derivatized recombinant animal somatotropin The efficacy of various modified (substituted) or derivatized recombinant animal somatotropins of the present invention for altering the growth rate of animals is determined utilizing a hypophysectomized (hypox) rat assay. The hypophysectomized rat does not produce its own growth hormone and is sensitive to injected bovine growth hormone. The response measured is growth over a period of time such as 10 days.

Each of the hypox albino rats (Taconic Farms, Sprague Dawley derived is injected with a sufficient quantity of compositions prepared in Example XX to provide a 10-day dose of 800 micrograms (80 micrograms/day) of porcine growth hormone in 0.2 ml of the formulation listed. Alternatively, each of the hypox albino rats are injected daily with 80 micrograms of porcine growth hormone derivative.
Test Procedures Prior to the test, the animals are weighed and the animals to be used for the test are selected based on body weight. Only those animals whose body weights are one standard deviation from the mean body weight of the group are selected. The resulting group is then randomly divided into treatment groups consisting of eight rats/group by a computer generated randomization procedure. The test animals are then transferred to a clean cage and housed four rats/cage. On the initial day of the study the test animals are weighed and any animals with excessive weight gain or loss (±5 grams) are replaced. The animals are then assigned to test groups and treated.

At the end of the ten-day test period, total weight gain for each animal is recorded and the average weight gain per rat for each treatment determined. The results of these experiments, which are summarized in

| Hypox Rat Data derivative | gms growth | | | | |
|---|---|---|---|---|---|
| | 0–2 days | 2–4 days | 4–7 days | 7–10 days | total |
| rpST | 7.5 | 5.6 | 6.8 | 10.1 | 30 |
| (Cam-Cys 183, 191)rpST | 7.6 | 5.3 | 8.4 | 8.4 | 29.7 |
| (Sulfite-Cys 183, 191) rpST | 8.9 | 4.8 | 11.1 | 8.1 | 32.9 |
| (Ala 183, 191)rpST | 7.1 | 6.3 | 9.3 | 6.5 | 29.2 |
| (SCH$_3$-Cys 183, 191)rpST | 7.0 | 6.4 | 6.9 | 9.5 | 29.8 |
| (S-CH$_2$COO$^-$-Cys 183, 191) rpST | 5.9 | 5.6 | 9.1 | 7.9 | 28.5 |
| (S-CH$_2$CH$_2$CH$_2$SO$_3^-$-Cys 183, 191)rpST | 6.9 | 5.3 | 6.8 | 9.0 | 28.0 |

From the above data it is seen that each of the modified or derivatized recombinant porcine somatotropins evaluated are biologically active and provided excellent growth of animals.

EXAMPLE 18

Carcass Evaluations of Pigs receiving derivatized recombinant porcine somatotropin Pigs are housed in individual pens. Initial weight of the pigs are approximately 60 kg. Pigs are slaughtered at an average live weight of 100 kg. Injections at the base of the ear of test compositions are initiated after a 4 day adjustment period. The pigs are fed the standard "Cy Hog ration" ad libitum and water is provided ad libitum.

Growth performance is determined on a weekly basis. The following data are collected: average daily gain, average daily feed intake and feed efficiency.

After approximately a 40 kg gain, the pigs are slaughtered and the carcasses evaluated. The following data are collected at slaughter: hot carcass weight, semitendinosis weight, organ (liver, kidney, heart) weights and leaf fat weight. After a 24 hour chill, the following measurements are recorded: carcass length, backfat depth (first rib, last rib, last lumbar vertebrae, three-quarter depth at the tenth rib, P-2), belly thickness, loin eye area, color, firmness, marbling and muscle score.

In this evaluation a negative control receives a daily injection of saline, CAM-rPST is (Cam-Cys 183,191)rpST described in Example 7 above and the positive control receives a daily injection of native PST.

CARCASS EVALUATION–(Cam-Cys 183,191)rPST

Six pigs per treatment are individually housed and administered their respective treatment from 44 to 94 kg liveweight. Growth and selected carcass data are presented below along with calculations of relative efficiency.

Effects of Carbamidomethylated-rpST (CAM-rpST) on Growth Performance and Selected Carcass Characteristics of Finishing Pigs (Least-squares Means)

| Criterion | Neg Cont | CAM-rpST | Pos Cont |
|---|---|---|---|
| Avg daiy gain, kg | .99 | 1.07 | 1.09 |
| Avg daily feed intake, kg | 3.11 | 3.03 | 2.75 |
| Gain/Feed | .32 | .35 | .40 |
| Liver, g | 1726.1 | 1892.8 | 2085.5 |
| Leaf fat, | 762.4 | 765.5 | 563.3 |
| Tenth rib backfat, cm | 2.22 | 2.00 | 1.88 |
| P-2 backfat, cm | 1.80 | 1.50 | 1.45 |
| Semitendinosis weight, g | 359.5 | 353.1 | 387.9 |
| Loin eye area, cm$^2$ | 38.6 | 39.0 | 39.6 |

EXAMPLE 19

Nitrogen Balance Experiments Conducted with (Cam-Cys 183,191)rpST

Pigs are housed in individual stainless steel metabolism crates. Injections at the base of the ear are initiated when the pigs are put into the crates. The pigs are allowed a five day period to adjust to the new environment. During this period, feed intake is monitored and adjusted such that all pigs consume the same amount of feed each day (Cy Hog ration, 18% crude protein). Collection of feces and urine begins after at least three days of constant intake. Pigs are fed equal amounts twice daily and water is provided ad libitum.

Total feces and urine are collected for five days (collections made each morning). In order to reduce N loss, 35 ml of 6N HCl is added to plastic urine collection buckets at the start of the collection phase of the experiment and after each daily collection. Care is taken to avoid any possible urine loss. The collected urine is diluted to a constant, recorded volume and then sampled (50 ml), labeled and frozen until analysis. Feces are collected daily, placed in labeled plastic bags and frozen until analysis. Orts are also collected, weighed and frozen. Small samples of feed are taken daily, frozen and pooled prior to analysis.

Feed and feces samples are dried overnight at 100° C. (or longer at a cooler temperature). The dried feed and feces samples are ground through a Wiley mill and allowed 2 days to air equilibrate. Dry matter and N content of the feed and feces are determined. All samples are analyzed for nitrogen using an automated Kjeldahl procedure. Urine is analyzed as is and the total daily urinary nitrogen excretion determined. Except for urine, all N values are expressed on a dry matter basis.

Pig weights are recorded on the first day of adjustment, on the first day of collection and upon completion of the collection phase. This ensures that the pigs are in positive energy balance.
Nitrogen Balance The evaluation of CAM-rPST in a nitrogen balance study involved a total of 12 growing pigs on three treatments: 1, negative control (daily saline injection); 2, CAM-rPST, 3 mg/d; and 3, positive control, 3 mg "native" PST. Feces and urine were collected for seven days following a 2 week adjustment period. The results and relative activity calculations are as follows:
Effects of Carbamidomethylated-rpST (CAM-rpST) and "Native" PST on the Nitrogen Balance of Growing Pigs.

| Criterion | Neg Cont | CAM-rpST | Pos Cont |
|---|---|---|---|
| Nitrogen intake, g/d | 41.86 | 41.36 | 41.83 |
| Nitrogen excretion, | | | |
| g/d feces | 5.25 | 5.21 | 4.65 |
| urine | 23.06 | 16.74 | 15.12 |
| Nitrogen absorbed, g/d | 36.61 | 6.15 | 37.18 |
| Nitrogen digestibility, % | 87.46 | 87.43 | 88.88 |
| Nitrogen retention, g/d | 13.56 | 19.41 | 22.06 |
| Average daily gain, g | 328.6 | 383.9 | 401.8 |

*CAM-PST = (Cam-Cys 183, 191)rPST

EXAMPLE 20

Preparation of paste using (Cam-Cys $^{183,191}$)rpST

A mixture of (Cam-Cys $^{183,191}$)rpST containing sodium benzoate (7% w/w) and a block copolymer of ethylene oxide and propylene oxide (0.5% w/w) is prepared by the spray drying procedure described in Example 13.

The thus prepared mixture (7.28 g) is added to a stirred solution of glyceryl tristearate (19.5 g) in a 4/1 w/w mixture of, a mixture of caprylic, capric, lauric and caproic triglycerides (Miglyol, 813)³/soya oil (71 mL), at 75° C. to 80° C. The mixture is stirred at 75° C. to 80° C. until it is homogeneous and is then cooled. The resulting composition which is comprised on a weight basis of: (Cam-Cys $^{183,191}$) rpST 6.96%, sodium benzoate 0.51%, surfactant (block copolymer) 0.03% and vehicle 73.0%, is generally administered to animals, by subcutaneous injection, under the skin of said animals in the region of the head or neck.

EXAMPLE 21

Preparation of a viscous injectable gel formulation containing (Ala-Cys $^{183,191}$)rpST To 140 g of super refined soybean oil in a beaker, is added, 12 g of aluminum monostearate. The mixture is stirred until uniform and heated over 30 minutes to approximately 140°<C., when the apparent solution of the monostearate in the soybean oil occurs. The beaker is removed from the heater and allowed to cool to approximately 60°<C. Spray dried (Ala-Cys $^{183,191}$)rpST (2.66 g) is than added to it with stirring to produce a homogeneously distributed suspension. The viscous mixture is filled in 30 mL disposable syringes. The volume filled in each syringe is 20 mL, which contains 350 mg of (Ala-Cys $^{183,191}$)rpST. After filling the gel mixture into the syringes, the composition set to a creamy, rigid, but extrudable gel. The packed syringes are then stored in a refrigerator prior to use.

EXAMPLE 22

Preparation of paste using Ala-Cys $^{183,191}$ rPST

Sesame oil (4.18 g) and Gelucire 46/07 (Cattlefosse-0.74 gm) are mixed in a glass container using a stir bar. This is then heated to 65° C., with stirring until homogeneous. The stir bar is removed, and 0.052 g of Ala-Cys $^{183,191}$ rPST is added to provide the formulation.

EXAMPLE 23

Preparation of Zinc associated Ala-Cys $^{183,191}$ rPST and paste thereof

Ala-Cys $^{183,191}$ rPST is dissolved in 0.09M TRIS solution at 21.5 mg rPST per ml, 40° C. and pH 9.5. This is converted to the Zinc salt by adding 1M $ZnCl_2$ while stirring. The Zinc salt precipitates. It is recovered by centrifuging at 10,000×g for 30 min, maintaining the solution at 40° C. This is lyophilized to give a powder. To 140 g of sesame oil in a beaker are added 12 g of aluminum monostearate. The contents are heated at 155° C. with stirring (until the monosterate is dissolved). The beaker is removed from the heater and allowed to cool. On cooling, the solution becomes a gel. The gel is fed into a ball mill (equiped with a high shear agitator and stainless steel balls). Vacuum is applied to the mill, and the Zinc powder added slowly until the composition contained 40% of the Zinc powder. Stirring continued until the median diameter of the Zinc powder is reduced to under 10 microns. The steel balls are moved from the gel, which is put into syringes.

The DNA strains referred to hereinabove were deposited in the ATCC on Aug. 23, 1988. They are mp11pSTE34 (ATCC number 40482), pRO211 (ATCC number 40483) and pig24 (ATCC number 40484). It is recognized by those skilled in the art that these DNAs can be inserted into any appropriate expression system to obtain the somatotropins of the invention or mutations thereof.

The E. coli K12 bacterial strains expressing some of the novel animal somatotropins of the present invention also were deposited in the ATCC on Aug. 23, 1988. The bacterial strains include E. coli strain 1655 (ATCC number 67762), 1655/pROpSTA34 (ATCC number 67763), 1655/pROpSTE34 (ATCC number 67764), 1655/pROpST (ATCC number 67765), 4200 (ATCC number 67766), 4200/pROpSTA34 (ATCC number 67767), 4200/pROpSTE34 (ATCC number 67768), 420/pROpST (ATCC number 67769), 4255 (ATCC number 67770), 4255/pROpSTA34 (ATCC number 67771), 4255/pROpSTE34 (ATCC number 67772), 4255/pROpST (ATCC number 67773) and 4300 (ATCC number 67774).

EXAMPLE 24

Deletion of the Cysteines in the small loop disulphide bond using two sysnthetic oligonucleotides A synthetic olignucleotide designated C183del has the following sequence:

5' CGG GTC ATG AAG AGA CGC TTC GTG GAG 3'

This oligonucleotide differs from the analogous DNA sequence of the rpST gene in two respects. First, the DNA encoding the cysteine condon at position 183 is deleted in the oligonucleotide. Second, the DNA encoding the arginine condon at position 184 is changed from CGC to AGA in the oligonucleotide, the latter of which also encodes arginine. Thereofre, the cysteine present at position 183 is deleted.

Single stranded pGEM-3z(f+)pST-SX DNA is the substrate for mutagenesis. This DNA is composed of a modified rpST gene contained in the commercially available phagemid, pGEM-3z(f+). The modification of the rpST gene results in the alteration of the DNA sequence to allow for the introduction of a Sac I restriction endonuclease cleavage site at positions 225–230 of the coding reigon and for the introduction of an Xba I restriction endonuclease cleavage site at positions 285–290. These alterations in the DNA sequence do not change the amino acid sequence of the rpST protein. An ECoRI/Hind III fragment cleaved with these restriction endonucleases using standard procedures, resulting in phagemid pGEM-3z(f+)pST-SX. The single stranded pGEM-3z(f+) DNA is prepared from purified phage by standard protocols/. 2000 ng of this DNA is mixed with 100 ng of the C183del oligonucleotide, the latter of which has been phosphorylated at its 5' end previously with adenosine 5' triphosphate and polynucleotide kinase. The mixture is contained in a total volume of 10 ml in 1× annealing buffer (lX annealing buffer is 75 mM KCl and 5 mM Tris-Cl, pH8.0). The mixture is heated at 65° C. for 7 minutes followed by a 10 minute incubation at room temperature. This procedure permits the oligonucelotide to anneal to the single stranded substrate DNA. Annealed molecules are converted to covalently closed, double stranded DNA by the addition of 22 ml H20, ml 20 mM ATP, 2 units each of T4 DNA ligase, and DNA polymerase I large fragment (for unit definition, see New England Biolabs catalogue, 1986), 2 ml 20× dNTP's (a mixture of the four deoxyribonucleotide 5' triphosphates each at a concentration of 2 mM) and 4 ml 10× fill in buffer (1× fill in buffer is 27.5 mM Tris-Cl pH 7.5, 15 mM MgCl2, 2 mM DDT). After a one hour incubation at room temperature, half of the reaction is introduced into HB101 competent cells by a standard transformation protocol. After overnight incubation at 37° C., colonies are transferred onto nitrocellulose filters and processed for hybridization by detection of the desired mutation by radio-labelling its 5' end with gamma-32P-ATP and oligoucleotide kinase. After a three hour prehybridization at 37° C. in 5× SSC, 1× Denhardt's and 150 ug/ml yeast tRNA, the radio-labelled oligonucleotide is added and allowed to hybridize with the DNA on the filters overnight at 37° C. The filters are washed for 30 minutes at 37° C. in 5× SSC, followed by a 30 minute wash in TAC at 61.5° C. During this latter wash, only those colonies whose plasmid DNA contains the desired mutation will continue to hybridize with the radio-labelled oligonucleotide probe. These colonies are detected after exposure of the washed filters to X-ray film. Plasmid DNA is prepared from several of these colonies from the original petri plate, introduced into HB101 competent cells as descrived previously, and rescreened with the radiolabelled oligonucleotide probe as above. Plasmid DNA is prepared from colonies whose DNA hybridizes with the probe and are analyzed for the desired DNA sequence. All clones analyzed contain the C183del mutation. Plasmid DNA from one clone, designated pGEM-3z(f+)pST-SXC183del, is introduced into JM101 competent cells by transformation and single stranded DNA is prepared from purified phage derived from a single transformant.

To delete the cysteine-encoding DNA at position 191, the following oligonucleotide, designated c191del, is synthesized:

5' TTC GTG GAG AGC TCG TTC TAG TTG 3'

This oligonucleotide differs from the analogous DNA in the rpST gene in two respects. First, the DNA encoding the cysteine condon at position 191 is deleted in the oligonucleotide. Second, the serine-encoding DNA at position 190 has been changed from ABC to TCG in the oligonucleotide, the latter of which also encodes serince.

The template single stranded DNA from pGEM-3z(f+) pST-SXC183del and the C191del oligonucleotide are annealed, extended and ligated as before. The mixture is introduced into HA101 comnetent cells and transformants are analyzed for the presence of the mutation exactly as described for C183del. The C191del oligonucleotide is used as the reaiolabelled detection probe. Hybridization and washing conditions are exactly as described for C183del. Several clones containing the C191del mutation are identified from DNA sequence analysis. Plasmid DNA containing the C183 and C191 deletions is designated pGEM-3z-(f+)-pST-SXC183, 191del.

What is claimed is:

1. A recombinant, nonhuman animal somatotropin in which at least one small loop cysteine amino acid residue in said recombinant animal somatotropin is replaced or eliminated such that said animal somatotropin is stabilized in a sustained release form.

2. A recombinant animal somatotropin according to claim 1, wherein said at least one small loop cysteine residue is replaced by an amino acid selected from arginine, lysine, aspartic acid, glutamic acid, asparagine, glutamine, histidine, alanine, glycine, isoleucine, leucine, valine, phenylalanine, tryptophan, tyrosine, methionine, serine, threonine and proline, wherein each replacement need not be with identical amino acids.

3. A modified recombinant animal somatotropin according to claim 1, wherein said animal somatotropin is (Ala $^{183,191}$)rpST; (Ala $^{183,191}$)rbST; (Ala $^{183,191}$)roST; (Ala $^{183,191}$)raST; (Ser $^{183,191}$)rpST; (Ser $^{183,191}$)rbST; (Ser $^{183,191}$)roST; (Ser $^{183,191}$)raST; (Glu $^{183,191}$)rpST; (Glu $^{183,191}$)rbST; (Glu $^{183,191}$)roST; (Glu $^{183,191}$)raST; (Glu $^{183}$-Ala $^{191}$)rpST; (Glu $^{183}$-Ala $^{191}$)rbST; (Glu $^{183}$-Ala $^{191}$)roST; (Glu $^{183}$-Ala $^{191}$)raST; (Glu $^{183}$-Ser $^{191}$)rpST; (Glu $^{183}$-Ser $^{191}$)rbST; (Glu $^{183}$-Ser $^{191}$)roST; (Glu 183-Ser $^{191}$)raST; (Arg $^{183,19}$)rpST; (Trp $^{183,191}$)rpST; (Asp $^{183,191}$)rpST and (Asn $^{183,191}$)rpST.

4. A recombinant, nonhuman animal somatotropin according to claim 1, which is capable of remaining in a solubilized monomeric form longer than natural animal somatotropin.

5. A recombinant, nonhuman animal somatotropin according to claim 1, which, upon solubilization, is essentially free of aggregation due to dimer formation.

6. A recombinant, nonhuman animal somatotropin according to claim 1, wherein two small loop cysteine residues are replaced or eliminated.

7. A recombinant, nonhuman animal somatotropin according to claim 1, wherein at least one small loop cysteine residue is eliminated.

8. A pharmaceutical composition comprising: a recombinant animal somatotropin according to claim 1 wherein the cysteine amino acid residues located in the 183 and 191 position are replaced by amino acid residues individually selected from arginine, lysine, aspartic acid, glutanic acid, asparagine, glutamine, histidine, alanine, glycine, isoleucine, leucine, valine, phenylalanine, typtophan, tyrosine, methionine, serine, threonine or proline.

9. A pharmaceutical composition comprising: a recombinant animal somatotropin according to claim 1 wherein the cysteine amino acid residue located at 183 or 191 or both positions is deleted.

10. A composition comprising: (i) a growth promoting amount of a recombinant, nonhuman animal somatotropin having at least one small loop cysteine replaced or eliminated such that said recombinant animal somatotropin is stabilized in a sustained release form or (ii) a pharmaceutically acceptable salt thereof; and a pharmaceutically acceptable solid or liquid carrier therefore, wherein said composition is effective in increasing the growth rate of an animal over an extended period of time.

11. A composition according to claim 10, wherein said composition is capable of being parenterally administered to said animal.

12. A composition according to claim 10, wherein said recombinant, nonhuman animal somatotropin is capable of remaining in a solubilized monomeric form longer than natural animal somatotropin.

13. A composition according to claim 10, wherein said recombinant, nonhuman animal somatotropin, when solubilized, is essentially free of aggregation due to dimer formation.

14. A composition according to claim 10, wherein two small loop cysteine residues are replaced or eliminated.

15. A composition according to claim 10, wherein the composition is in a sustained release form, which can release active recombinant animal somatotropin over a sustained period.

16. A composition according to claim 10, wherein the composition is an implant.

17. A method for inhibiting aggregation of recombinant, nonhuman animal somatotropin, said method comprising: replacing at least one small loop cysteine amino acid residue of said recombinant animal somatotropin with an amino acid residue selected from arginine, lysine, aspartic acid, glutamic acid, asparagine, glutamine, histidine, alanine, glycine, isoleucine, leucine, valine, phenylalanine, tryptophan, tyrosine, methionine, serine, threonine and proline, wherein each replacement need not be with identical amino acids.

18. A method according to claim 17, wherein one (1) or two (2) of the cysteines in the small loop of said somatotropin, are replaced by amino acids selected from alanine, serine, glutamic acid, arginine, tryptophan and asparagine, and the cysteines at the 55 and 166 positions in the large loop are not replaced.

19. A method for inhibiting aggregation of a recombinant, nonhuman animal somatotropin, said method comprising: deleting at least one of the cysteine amino acid residues of the small loop of said recombinant animal somatotropin.

\* \* \* \* \*

UNITED STATES PATENT AND TRADEMARK OFFICE
CERTIFICATE OF CORRECTION

PATENT NO. : 5,891,840
DATED : April 6, 1999
INVENTOR(S) : Susan Mancini Cady, et al.

It is certified that error appears in the above-identified patent and that said Letters Patent is hereby corrected as shown below:

Column 3, delete lines 21-26 in its entirety.

Column 4, line 1, change "FIG. 4" to --FIG. 3--.

Column 4, line 5, change "FIG. 5" to --FIG. 4--.

Column 11, lines 54 and 55, replace the sentence "The DNA sequence is illustrated in FIG. 3." with --DNA sequence analysis of M13p11ST-single stranded DNA and M13mp11pST34-single stranded reveal that for the former positions 183 and 191 are Cys(TGT), while for the latter PST, position 183 is Ala (GCG) and position 191 is Ala (GCT).--

Signed and Sealed this

Ninth Day of November, 1999

Attest:

Q. TODD DICKINSON

*Attesting Officer*  *Acting Commissioner of Patents and Trademarks*